(12) United States Patent
Vanhasebroeck et al.

(10) Patent No.: US 7,422,886 B2
(45) Date of Patent: Sep. 9, 2008

(54) METHOD FOR DETERMINING MODULATION OF P110Δ ACTIVITY

(75) Inventors: Bart Vanhasebroeck, London (GB); Michael Derek Waterfield, London (GB)

(73) Assignee: Ludwig Institute for Cancer Research, New York, NY (US)

( * ) Notice: Subject to any disclaimer, the term of this patent is extended or adjusted under 35 U.S.C. 154(b) by 315 days.

(21) Appl. No.: 11/219,611

(22) Filed: Sep. 2, 2005

(65) Prior Publication Data

US 2006/0018893 A1    Jan. 26, 2006

Related U.S. Application Data

(62) Division of application No. 10/922,748, filed on Aug. 20, 2004, now abandoned, which is a division of application No. 10/162,160, filed on Jun. 3, 2002, now Pat. No. 6,849,420, which is a division of application No. 09/194,640, filed on Dec. 1, 1998, now Pat. No. 6,482,623.

(30) Foreign Application Priority Data

Jun. 1, 1996 (GB) ................... 9611460.8

(51) Int. Cl.
*C12N 9/14* (2006.01)
*C07K 1/00* (2006.01)
*C07H 21/04* (2006.01)

(52) U.S. Cl. ............... 435/194; 530/350; 530/300; 536/23.2; 536/23.5

(58) Field of Classification Search ............ 435/194; 530/350, 300; 536/23.2, 23.5
See application file for complete search history.

(56) References Cited

U.S. PATENT DOCUMENTS 6,482,623 B1 * 11/2002 Vanhaesebroeck et al. .. 435/194
6,849,420 B2 * 2/2005 Vanhaesebroeck et al. ...... 435/21

* cited by examiner

*Primary Examiner*—Rebecca E. Prouty
*Assistant Examiner*—Malgorzata A Walicka
(74) *Attorney, Agent, or Firm*—Fulbright & Jaworski LLP

(57) ABSTRACT

The invention relates to a novel lipid kinase which is part of the PI3 Kinase family. PI3 Kinases catalyze the addition of phosphate to inositol generating inositol mono, di and triphosphate. Inositol phosphates have been implicated in regulating intracellular signaling cascades resulting in alternations in gene expression which, amongst other effects, can result in cytoskeletal remodeling and modulation of cellular motility. More particularly the invention relates to a novel human PI3 Kinase, p110Δ which interacts with p85, has a broad phosphinositide specificity and is sensitive to the same kinase inhibitors as PI3 Kinase p110A. However, in contrast to previously identified PI3 Kinases which show a ubiquitous pattern of expression, p110Δ is selectively expressed in leucocytes. Importantly, p110Δ shows enhanced expression in most melanomas tested and therefore may play a crucial role in regulating the metastatic property exhibited by melanomas. The identification of agents that enhance or reduce p110Δ activity may therefore prevent cancer metastatis.

6 Claims, 16 Drawing Sheets

FIG. 1A

Figure 1B:
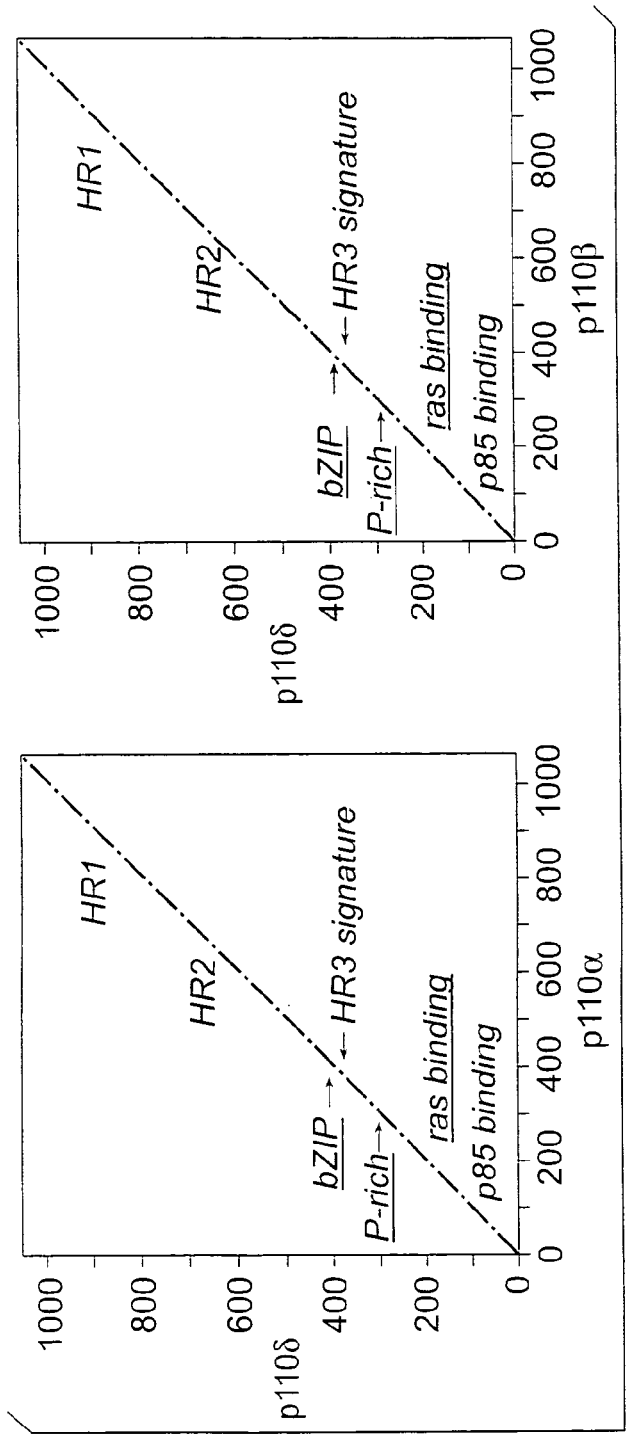

```
   1 MPPGVDCPME FWTKEENQSV VVDFLLPTGV YLNFPVSRNA NLSTIKQLLW HRAQYEPLFH MLSGPEAYVF TCINQTAEQQ ELEDEQRRLC DVQPFLPVLR
 101 LVAREGDRVK KLINSQISLL IGKGLHEFDS LCDPEVNDFR AKMCQFCEEA AARRQQLGWE AWLQYSFPLQ LEPSAQTWGP GTLRLPNRAL LVNVKFEGSE
 201 ESFTFQVSTK DVPLALMACA LRKKATVFRQ PLVEQPEDYT LQVNGRHEYL YGSYPLCQFQ YICSCLHSGL TPHLTMVHSS SILAMRDEQS NPAPQVQKPR
 301 AKPPPIPAKK PSSVSLWSLE QPFFRIELIQG SKVNADERMK LVVQAGLFHG NEMLCKTVSS SEVSVCSEPV WKQRLEFDIN ICDLPRMARL CFALYAVIEK
 401 AKKARSTKKK SKKADCPIAW ANLMLFDYKD QLKTGERCLY MWPSVPDEKG ELLNPTGTVR LLICLPEVAP HPVYYPALEK ILELGRHSEC
 501 VHVTEEEQLQ LREILERRGS GELYEHEKDL VWKLRHEVQE HFPEALARLL LVTKWNKHED VAQMLYLLCS WPELPVLSAL ELLDFSFPDC HVGSFAIKSL
 601 RKLTDDELFQ YLLQLVQVLK YESYLDCELT KFLLDRALAN RKIGHFLFWH LRSEMHVPSV ALRFGLIIEA YCRGRTHHMK VIMKQGEALS KLKALNDFVK
 701 LSSQKTPKPQ TKELMHLCMR QEAYLEALSH LQSPLDPSTL LAEVCVEQCT FMDSKMKPLW IMYSNEEAGS GGSVGIIFKN GDDLRQDMLT LQMIQLMDVL
 801 WKQEGLDLRM TPYGCLPTGD RTGLIEVVLR SDTIANIQLN KSNMAATAAF NKDALLNWLK SKNPGEALDR AIEEFTLSCA GYCVATYVLG IGDRHSDNIM
 901 IRESGQLFHI DFGHFLGNFK TKFGINRERV PFILTYDFVH VIQQGKTNNS EKFERFRGYC ERAYTILRRH GLLFLHLFAL MRAAGLPELS CSKDIQYLKD
1001 SLALGKTEEE ALKHFRVKFN EALRESWKTK VNWLAHNVSK DNRQ
```

FIG. 5
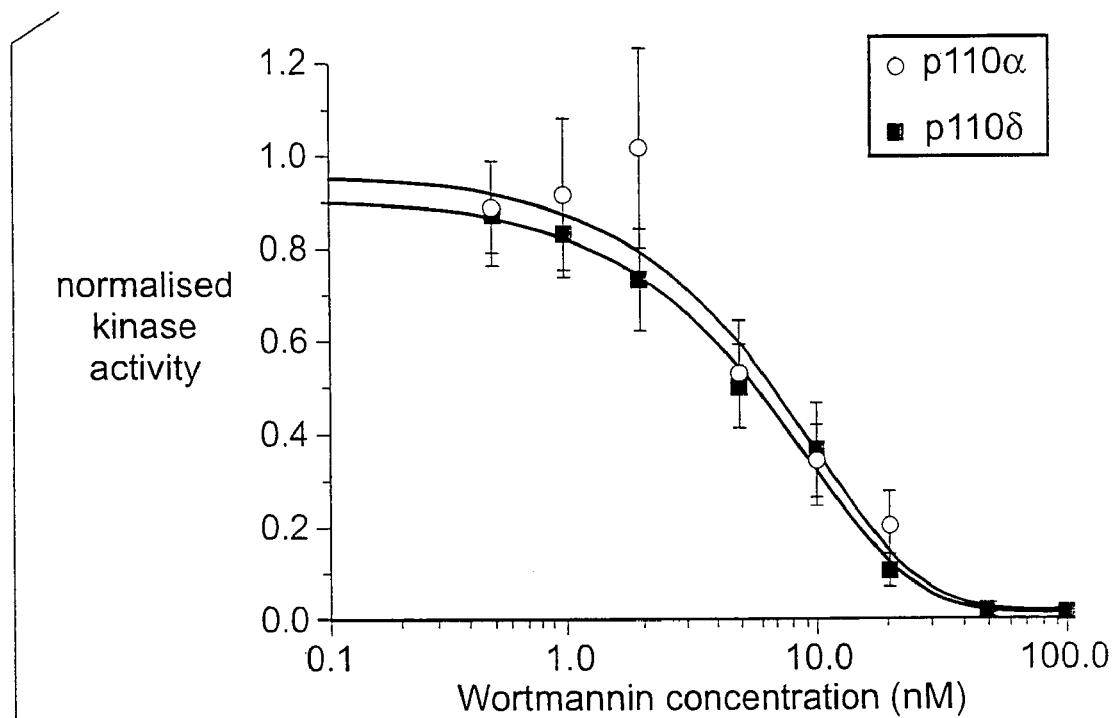
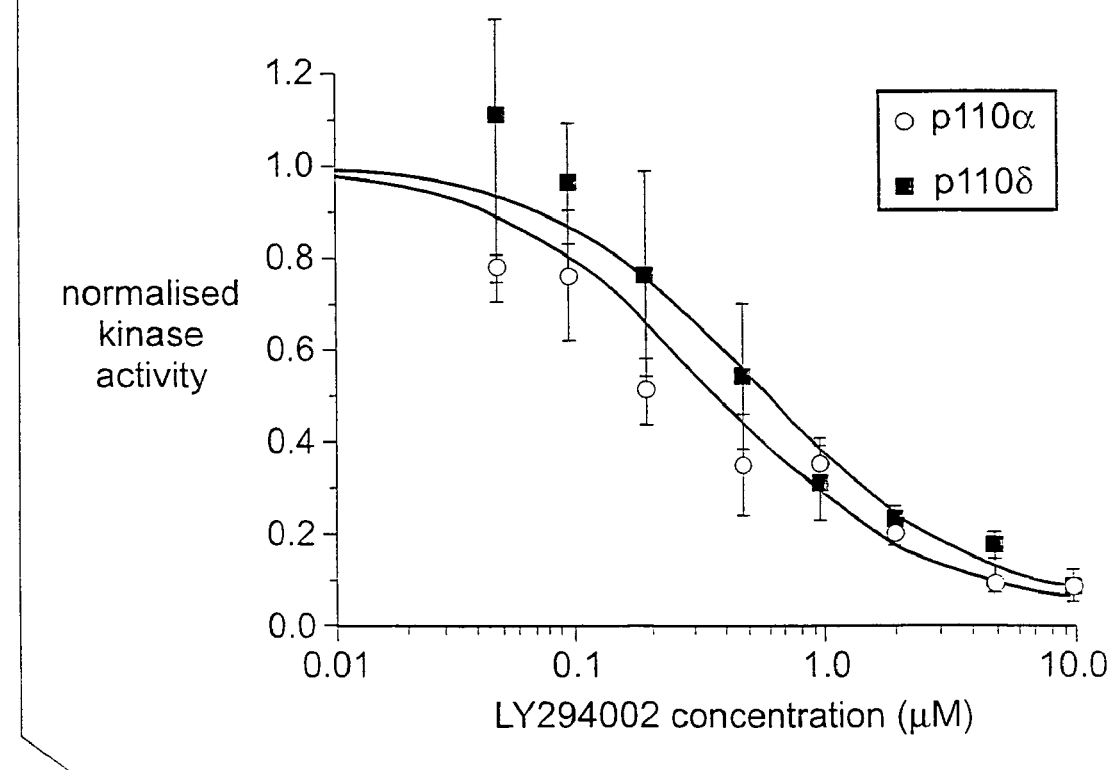

FIG. 9-A

```
   1 ATGCCCCCTG GGGTGGACTG CCCCATGGAA TTCTGGACCA AGGAGGAGAA
  51 TCAGAGCGTT GTGGTTGACT TCCTGCTGCC CACAGGGGTC TACCTGAACT
 101 TCCCTGTGTC CCGCAATGCC AACCTCAGCA CCATCAAGCA GCTGCTGTGG
 151 CACCGCGCCC AGTATGAGCC GCTCTTCCAC ATGCTCAGTG GCCCCGAGGC
 201 CTATGTGTTC ACCTGCATCA ACCAGACAGC GGAGCAGCAA GAGCTGGAGG
 251 ACGAGCAACG GCGTCTGTGT GACGTGCAGC CCTTCCTGCC CGTCCTGCGC
 301 CTGGTGGCCC GTGAGGGCGA CCGCGTGAAG AAGCTCATCA ACTCACAGAT
 351 CAGCCTCCTC ATCGGCAAAG GCCTCCACGA GTTTGACTCC TTGTGCGACC
 401 CAGAAGTGAA CGACTTTCGC GCCAAGATGT GCCAATTCTG CGAGGAGGCG
 451 GCCGCCCGCC GGCAGCAGCT GGGCTGGGAG GCCTGGCTGC AGTACAGTTT
 501 CCCCCTGCAG CTGGAGCCCT CGGCTCAAAC CTGGGGGCCT GGTACCCTGC
 551 GGCTCCCGAA CCGGGCCCTT CTGGTCAACG TTAAGTTTGA GGGCAGCGAG
 601 GAGAGCTTCA CCTTCCAGGT GTCCACCAAG GACGTGCCGC TGGCGCTGAT
 651 GGCCTGTGCC CTGCGGAAGA AGGCCACAGT GTTCCGGCAG CCGCTGGTGG
 701 AGCAGCCGGA AGACTACACG CTGCAGGTGA ACGGCAGGCA TGAGTACCTG
 751 TATGGCAGCT ACCCGCTCTG CCAGTTCCAG TACATCTGCA GCTGCCTGCA
 801 CAGTGGGTTG ACCCCTCACC TGACCATGGT CCATTCCTCC TCCATCCTCG
 851 CCATGCGGGA TGAGCAGAGC AACCCTGCCC CCAGGTCCA GAAACCGCGT
 901 GCCAAACCAC CTCCCATTCC TGCGAAGAAG CCTTCCTCTG TGTCCCTGTG
 951 GTCCCTGGAG CAGCCGTTCC GCATCGAGCT CATCCAGGGC AGCAAAGTGA
1001 ACGCCGACGA GCGGATGAAG CTGGTGGTGC AGGCCGGGCT TTTCCACGGC
1051 AACGAGATGC TGTGCAAGAC GGTGTCCAGC TCGGAGGTGA GCGTGTGCTC
1101 GGAGCCCGTG TGGAAGCAGC GGCTGGAGTT TGACATCAAC ATCTGCGACC
1151 TGCCCCGCAT GGCCCGTCTC TGCTTTGCGC TGTACGCCGT GATCGAGAAA
1201 GCCAAGAAGG CTCGCTCCAC CAAGAAGAAG TCCAAGAAGG CGGACTGCCC
1251 CATTGCCTGG GCCAACCTCA TGCTGTTTGA CTACAAGGAC CAGCTTAAGA
1301 CCGGGGAACG CTGCCTCTAC ATGTGGCCCT CCGTCCCAGA TGAGAAGGGC
1351 GAGCTGCTGA ACCCCACGGG CACTGTGCGC AGTAACCCCA ACACGGATAG
1401 CGCCGCTGCC CTGCTCATCT GCCTGCCCGA GGTGGCCCCG CACCCCGTGT
1451 ACTACCCCGC CCTGGAGAAG ATCTTGGAGC TGGGGCGACA CAGCGAGTGT
```

FIG. 9-B

```
1501  GTGCATGTCA CCGAGGAGGA GCAGCTGCAG CTGCGGGAAA TCCTGGAGCG
1551  GCGGGGGTCT GGGGAGCTGT ATGAGCACGA GAAGGACCTG GTGTGGAAGC
1601  TGCGGCATGA AGTCCAGGAG CACTTCCCGG AGGCGCTAGC CCGGCTGCTG
1651  CTGGTCACCA AGTGGAACAA GCATGAGGAT GTGGCCCAGA TGCTCTACCT
1701  GCTGTGCTCC TGGCCGGAGC TGCCCGTCCT GAGCGCCCTG GAGCTGCTAG
1751  ACTTCAGCTT CCCCGATTGC ACGTAGGCT CCTTCGCCAT CAAGTCGCTG
1801  CGGAAACTGA CGGACGATGA GCTGTTCCAG TACCTGCTGC AGCTGGTGCA
1851  GGTGCTCAAG TACGAGTCCT ACCTGGACTG CGAGCTGACC AAATTCCTGC
1901  TGGACCGGGC CCTGGCCAAC CGCAAGATCG CCACTTCCT TTTCTGGCAC
1951  CTCCGCTCCG AGATGCACGT GCCGTCGGTG GCCCTGCGCT TCGGCCTCAT
2001  CCTGGAGGCC TACTGCAGGG GCAGGACCCA CCACATGAAG GTGCTGATGA
2051  AGCAGGGGGA AGCACTGAGC AAACTGAAGG CCCTGAATGA CTTCGTCAAG
2101  CTGAGCTCTC AGAAGACCCC CAAGCCCCAG ACCAAGGAGC TGATGCACTT
2251  GTGCATGCGG CAGGAGGCCT ACCTAGAGGC CCTCTCCCAC CTGCAGTCCC
2301  CACTCGACCC CAGCACCCTG CTGGCTGAAG TCTGCGTGGA GCAGTGCACC
2351  TTCATGGACT CCAAGATGAA GCCCCTGTGG ATCATGTACA GCAACGAGGA
2401  GGCAGGCAGC GGCGGCAGCG TGGGCATCAT CTTTAAGAAC GGGGATGACC
2451  TCCGGCAGGA CATGCTGACC CTGCAGATGA TCCAGCTCAT GGACGTCCTG
2501  TGGAAGCAGG AGGGGCTGGA CCTGAGGATG ACCCCCTATG GCTGCCTCCC
2551  CACCGGGGAC CGCACAGGCC TCATTGAAG GGTACTCCGT TCAGACACCA
2601  TCGCCAACAT CCAACTCAAC AGAGCAACCT GGCAGCCACT AGCCGCCTTC
2651  TGGCCACATA TGTGCTGGGC ATTGGCGATC GGCACAGCGA ACACATCATG
2701  ATCCGAGAGA GTGGGCAGCT GTTCCACATT GATTTTGGCC ACTTTCTGGG
2751  GAATTTCAAG ACCAAGTTTG GAATCAACCG CGAGCGTGTC CCATTCATCC
2801  TCACCTACGA CTTTGTCCAT GTGATTCAGC AGGGGAAGAC TAATAATAGT
2851  GAGAAATTTG AACGGTTCCG GGGCTACTGT GAAAGGGCCT ACACCATCCT
2901  GCGGCGCCAC GGGCTTCTCT TCCTCCACCT CTTTGCCCTG ATGCGGGCGG
2951  CAGGCCTGCC TGAGCTCAGC TGCTCCAAAG ACATCCAGTA TCTCAAGGAC
3001  TCCCTGGCAC TGGGGAAAAC AGAGGAGGAG GCACTGAAGC ACTTCCGAGT
3051  GAAGTTTAAC GAAGCCCTCC GTGAGAGCTG GAAAACCAAA GTGAACTGGC
```

FIG. 9-C

```
3101  TGGCCCACAA CGTGTCCAAA GACAACAGGC AGTAGTGGCT CCTCCCAGCC
3151  CTGGGCCCAA GAGGAGGCGG CTGCGGGTCG TGGGGACCAA GCACATTGGT
3201  CCTAAAGGGG CTGAAGAGCC TGAACTGCAC CTAACGGGAA AGAACCGACA
3251  TGGCTGCCTT TTGTTTACAC TGGTTATTTA TTTATGACTT GAAATAGTTT
3301  AAGGAGCTAA ACAGCCATAA ACGGAAACGC CTCCTTCATG CAGCGGCGGT
3351  GCTGGGCCCC CCGAGGCTGC ACCTGGCTCT CGGCTGA
```

METHOD FOR DETERMINING MODULATION OF P110Δ ACTIVITY

This application is a divisional application of the U.S. application Ser. No. 10/922,748 filed Aug. 20, 2004, now abandoned, which is a divisional application of the U.S. application Ser. No. 10/162,160 filed Jun. 3, 2002, now U.S. Pat. No. 6,849,420, which is a divisional application of the U.S. application Ser. No. 09/194,640 filed Dec. 1, 1998, now U.S. Pat. No. 6,482,623.

The invention relates to a novel lipid kinase which is part of the PI3 Kinase (PI3K) family and more specifically the invention relates to various aspects of the novel lipid kinase particularly, but not exclusively, to an identification of expression of said kinase with a view to diagnosing or predicting motility or invasion of cells such as metastasis of cancer cells; and also agents for interfering with said expression or inhibiting said kinase with a view to enhancing or reducing or preventing said motility or invasion so as to enhance or restrict, respectively the movement of selected cells.

An overview of the PI3 kinase family of enzymes is given in our co-pending Patent Application WO93/21328. Briefly, this class of enzymes shows phosphoinositide (hereinafter referred to after as PI) 3-kinase activity. Following major advances in our knowledge of cell signal transduction and cell second messenger systems it is known that the PI3Ks have a major role to play in regulating cell function. Indeed, it is known that PI3Ks are members of a growing number of potential signalling proteins which associate with protein-tyrosine kinases activated either by ligand stimulation or as a consequence of cell transformation. Once thus associated they provide an important complex in the cell signalling pathway and thus direct events towards a given conclusion.

PI3 kinases catalyse the addition of phosphate to the 3'-OH position of the inositol ring of inositol lipids generating phosphatidyl inositol monophosphate, phosphatidyl inositol diphosphate and phosphatidyl inositol triphosphate (Whitman et al, 1988, Stephens et al 1989 and 1991). A family of PI3 kinase enzymes has now been identified in organisms as diverse as plants, slime molds, yeast, fruit flies and mammals (Zvelebil et al, 1996).

It is conceivable that different PI3 kinases are responsible for the generation of the different 3'-phosphorylated inositol lipids in vivo. Three classes of PI3 kinase can be discriminated on the basis of their in vitro lipid substrates specificity. Enzymes of a first class have a broad substrate specificity and phosphorylate PtdIns, PtdIns(4)P and PtdIns(4,5)$P_2$. Class I PI3 kinases include mammalian p110α, p110β and p110γ (Hiles et al, 1192; Hu et al, 1993; Stephens et al, 1994; Stoyanov et al, 1995).

P110α and p110β are closely related PI3 kinases which interact with p85 adaptor proteins and with GTP-bound Ras.

Two 85 kDa subunits, p85α and p85β, have been cloned (Otsu et al, 1992). These molecules contain an N-terminal src homology-3 (SH3) domain, a breakpoint cluster (bcr) homology region flanked by two proline-rich regions and two src homology-2 (SH2) domains. Shortened p85 proteins, generated by alternative splicing from the p85α gene or encoded by genes different from those of p85α/β, all lack the SH3 domain and the bcr region, which seem to be replaced by a unique short N-terminus (Pons et al, 1995; Inukai et al, 1996; Antonetti et al, 1996). The SH2 domains, present in all p85 molecules, provide the heterodimeric p85/p110 PI3Ks with the capacity to interact with phosphorylated tyrosine residues on a variety of receptors and other cellular proteins. In contrast to p110α and β, p110γ does not interact with p85 but instead associates with a p101 adaptor protein (Stephens et al, 1996). P110γ activity is stimulated by G-protein subunits.

PI3Ks of a second class contains enzymes which, at least in vitro, phosphorylate PtdIns and PtdIns(4)P but not PtdIns(4, 5)$P_2$ (MacDougall et al, 1995; Virbasius et al, 1996, Molz et al, 1996). These PI3Ks all contain a C2 domain at their C-terminus. The in vivo role of these class II PI3Ks is unknown.

A third class of PI3K has a substrate specificity restricted to PtdIns. These PI3Ks are homologous to yeast Vps34p which is involved in trafficking of newly formed proteins from the Golgi apparatus to the vacuole in yeast, the equivalent of the mammalian lysosome (Stack et al, 1995). Both yeast and mammalian Vps34p occur in a complex with Vps15p, a 150 kDa protein serine/threonine kinase (Stack et al, 1995; Volinia et al, 1995; Panaretou et al, submitted for publication).

PtdIns(3)P is constitutively present in cells and its levels are largely unaltered upon extracellular stimulation. In contrast, PtdIns(3, 4)$P_2$ and PtdIns(3, 4, 5)$P_3$ are almost absent in quiescent cells but are produced rapidly upon stimulation by a variety of growth factors, suggesting a likely function as second messengers (Stephens et al, 1993). The role of PI3Ks and their phosphorylated lipids in cellular physiology is just beginning to be understood. These lipids may fulfill a dual role: apart from exerting physical, charge-mediated effects on the curvature of the lipid bilayer, they also have the capacity to interact with specific binding proteins and modulate their localisation and/or activity. Amongst the potential targets for these lipids are protein kinases such as protein kinase C isoforms, protein kinase N/Rho-activated kinases and Akt/RAC/protein kinase B (Toker et al, 1994; Palmer et al, 1995; Burgering and Coffer, 1995; Franke et al, 1995; James et al, 1996; Klippel et al, 1996). Akt/RAC/protein kinase B is likely to be upstream of targets such as p70 S6 kinase and glycogen synthase kinase-3 (Chung et al, 1994; Cross et al, 1995). PI3Ks also affect the activity of small GTP-binding proteins such as Rac and Rab5, possibly by regulating nucleotide exchange (Hawkins et al, 1995; Li et al, 1996). Ultimately, the combination of these actions can result in cytoskeletal rearrangements, DNA synthesis/mitogenesis, cell survival and differentiation (Vanhaesebroeck et al, 1996).

We describe herein a mammalian novel Class I PI3 Kinase which we have termed p110δ. This novel PI3 Kinase typifies the Class I PI3 Kinase family in that it binds p85α, p85β and p85γ. In addition, it also binds GTP-ras but, like p110α, shows no binding of rho and rac. It also shares the same GTP-broad phosphoinositide lipid substrate specificity of p110α and p110β, and it also shows protein kinase activity and has a similar drug sensitivity to p110α.

However, it is characterised by its selective tissue distribution. In contrast to p110α and p110β which seem to be ubiquitously expressed, p110δ expression is particularly high in white blood cell populations i.e. spleen, thymus and especially peripheral blood leucocytes. In addition to this observation we have also found that p110δ is expressed in most melanomas, but not in any melanocytes, the normal cell counterpart of melanomas. Given the natural distribution of p110δ in tissues which are known to exhibit motility or invasion and also the expression of p110δ in cancer cells we consider that p110δ has a role to play in cell motility or invasion and thus the expression of this lipid kinase in cancer cells can explain the metastatic behaviour of cancer cells.

A further novel feature of p110δ is its ability to autophosphorylate in a $Mn^{2+}$-dependent manner. Indeed, we have shown that autophosphorylation tends to hinder the lipid kinase activity of the protein. In addition, p110δ contains distinct potential protein:protein interaction modules including a proline-rich region (see FIG. 1, position 292-311, wherein 8 out of 20 amino acids are proline) and a basic region leucine zipper (bZIP) like domain (Ing et al., 1994 and Hirai et al., 1996). Such biochemical and structural differences between p85-binding PI3 kinases indicate that they may fulfill distinct functional roles and/or be differentially regulated in vivo.

We disclose herein a nucleic acid molecule, of human origin, and corresponding amino acid sequence data relating to p110δ. Using this information it is possible to determine the expression of p110δ in various tissue types and in particular to determine the expression of same in cancer tissue with a view to diagnosing the motility or invasiveness of such tissue and thus predicting the potential for secondary tumours occurring. Moreover, it will also be possible to provide agents which impair the expression of p110δ or alternatively interfere with the functioning of same. For example, having regard to the sequence data provided herein it is possible to provide antisense material which prevents the expression of p110δ.

As mentioned above, the invention embraces antisense oligonucleotides that selectively bind to a nucleic acid molecule encoding a PI3Kδ protein, to decrease transcription and/or translation of PI3Kδ genes. This is desirable in virtually any medical condition wherein a reduction in PI3Kδ gene product expression is desirable, including to reduce any aspect of a tumor cell phenotype attributable to PI3Kδ gene expression. Antisense molecules, in this manner, can be used to slow down or arrest such aspects of a tumor cell phenotype.

As used herein, the term "antisense oligonucleotide" or "antisense" describes an oligoneucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the DNA sequence presented in FIG. 9 or upon allelic or homologous genomic and/or DNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 (Wagner et al., Nature Biotechnology 14:840-844, 1996) and more preferably, at least 15 consecutive bases which are complementary to the target. Most preferably, the antisense oligonucleotides comprise a complementary sequence of 20-30 bases. Although oligonucelotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5): 439457. 1994) and at which proteins are not expected to bind. Finally, although FIG. 9 discloses cDNA sequence, one of ordinary skill in the art may easily derive the genomic DNA corresponding to the cDNA of FIG. 9. Thus, the present invention also provides for antisense oligonucleotides which are complementary to the genomic DNA corresponding to FIG. 9. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing, to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., Nature Biotechnology 14:840-844, 1996). The present invention, thus, contemplates pharmaceutical preparations containing modified antisense molecules that are complementary to and hybridizable with, under physiological conditions, nucleic acids encoding PI3Kδ proteins, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

It is therefore an object of the invention to identify a novel PI3 Kinase and so provide means for predicting the likely motility or invasiveness of cells.

It is a yet further object of the invention to provide agents that enhance or reduce or prevent the expression of p110δ and/or agents which interfere with the functioning of p110δ, with a view to enhancing or hindering or preventing, respectively, the motility or invasiveness of cells.

According to a first aspect of the invention there is therefore provided an isolated autophosphorylating polypeptide which possesses PI3 kinase activity.

Ideally said polypeptide is derived from white blood cells and is typically expressed in melanomas, more ideally still said polypeptide is of human origin.

Moreover, the polypeptide is capable of association with p85 subunits of mammalian PI3 Kinases ideally to produce active complexes.

More preferably still the polypeptide has the amino acid sequence shown in FIG. 1A or a sequence homologous thereto which is in particularly characterised by a proline rich domain.

Reference herein to the term homologous is intended to cover material of a similar nature or of common descent or pocessing those features, as herein described, that characterise the protein, or material, whose corresponding nucleic acid molecule hybridises, such as under stringent conditions, to the nucleic acid molecule shown in FIG. 9. Typical hybridisation conditions would include 50% formamide, 5×SSPE, 5× Denhardts solution, 0.2% SDS, 200 μg/ml denatured sonicated herring sperm DNA and 200 μg/ml yeast RNA at a temperature of 60° C., (conditions described in the published patent specification WO 93/21328).

Ideally the polypeptide is produced using recombinant technology and is typically of human origin.

According to a further aspect of the invention there is provided an antibody to at least a part of the polypeptide of the invention, which antibody may be polyclonal or monoclonal.

According to a further aspect of the invention there is provided the whole or a part of the nucleic acid molecule shown in FIG. 9 which molecule encodes an autophosphorylating polypeptide having PI3 Kinase activity.

In the instance where said part of said molecule is provided, the part will be selected having regard to its purpose, for example it may be desirable to select a part having kinase activity for subsequent use or another part which is most suitable for antibody production.

According to a further aspect of the invention there is provided a nucleic acid molecule construct comprising a whole or a part of the nucleic acid molecule of the invention wherein the latter nucleic acid molecule is under the control of a control sequence and in appropriate reading frame so as to ensure expression of the corresponding protein.

According to a yet further aspect of the invention there is provided host cells which have been transformed, ideally using the construct of the invention, so as to include a whole or a part of the nucleic acid molecule shown in FIG. 9 so as to permit expression of a whole, or a significant part, of the corresponding polypeptide.

Ideally these host cells are eukaryotic cells for example, insect cells such as cells from the species *Spodoptera frugiperda* using the baculovirus expression system. This expression system is favoured in the instance where post translation modification is required. If such modification is not required a prokaryotic system may be used.

According to a further aspect of the invention there is provided a method for diagnosing the motility of cells comprising examining a sample of said cells for the expression of the polypeptide of the invention.

Ideally, investigations are undertaken in order to establish whether mRNA corresponding to the polypeptide of the invention is expressed in said cells, for e.g. by using PCR techniques or Northern Blot analysis. Alternatively, any other conventional technique may be undertaken in order to identify said expression.

According to a yet further aspect of the invention there is provided a method for identifying antagonists effective at blocking the activity of the polypeptide of the invention which comprises screening candidate molecules for such activity using the polypeptide, or fragments thereof the invention.

Ideally, screening may involve artificial techniques such as computer-aided techniques or conventional laboratory techniques.

Ideally, the above method is undertaken by exposing cells known to express the polypeptide of the invention, either naturally or by virtue of transfection, to the appropriate antagonist and then monitoring the motility of same.

Alternatively, the method of the invention may involve competitive binding assays in order to identify agents that selectively and ideally irreversibly bind to the polypeptide of the invention.

According to a yet further aspect of the invention there is provided a pharmaceutical or veterinary composition comprising an agent effective at enhancing or blocking the activity or expression of the polypeptide of the invention which has been formulated for pharmaceutical or veterinary use and which optionally also includes a dilutant, carrier or excipient and/or is in unit dosage form.

According to a yet further aspect of the invention there is provided a method for controlling the motility of cells comprising exposing a population of said cells to either an agonist or antagonist or the polypeptide of the invention or to antisense material as herein described.

Alternatively, in the aforementioned method said cells may be exposed alternatively or additionally, to the polypeptide of the invention with a view to increasing the effective levels of said polypeptide and so enhancing cell motility.

The aforementioned method may be undertaken either in vivo or in vitro.

According to a yet further aspect of the invention there is provided use of an agent effective at blocking the activity of the polypeptide of the invention for controlling cell motility.

According to a yet further aspect of the invention there is provided use of the polypeptide of the invention for enhancing cell motility.

According to a yet further aspect of the invention there is provided antisense oligonucleotides ideally modified as herein described, for hybridizing to the nucleic acid of the invention.

An embodiment of the invention will now be described by way of example only with reference to the following figures, materials and methods wherein:

FIG. 1(A) shows translated amino acid sequence of human p110δ cDNA. The proline-rich region and the bZIP-like domain are indicated by open and shaded box, respectively.

(B) Dotplot comparison of the full length amino acid sequence of p110δ with that of p110α and p110β. Non-conserved sequence motifs are underlined. Dotplot comparisons were performed using the COMPARE program (UWGCG package: Devereux et al, 1984). (C) Comparison of the p110δ amino acid sequence flanking HR3 with respective homologous regions of p110α and p110β. Amino acid numbering is that of p110δ. Proline-rich region: critical prolines enabling the formation of a left-handed polyproline type-II helix in p110δ are indicated with an asterisk bZIP region: conserved L/V/I residues of the leucine-zipper region are indicated with arrowheads.

FIG. 2. Interaction of p110δ with p85 and Ras (A) Insect cells were infected with recombinant baculovirus encoding GST-p110δ, alone or in combination with viruses encoding either p85α, β or γ. After 2 days, GST-p110δ was affinity-purified from the cell lysates using glutathione-sepharose, washed, and analysed by SDS-PAGE and Coomassie staining. (B) P110δ was immunoprecipitated from 500 μg human neutrophil cytosol and probed for the presence of different p85 isoforms by Western blotting. rec=recombinant p85 purified from Sf9 cells. (C) GST-p110α/85α and GST-p110δ/85α (0.25 μg) were incubated with the indicated amount (in μg) of GTP- or GDP-loaded V12-Ras, washed and probed for the presence of Ras by Western blotting as described (Rodriguez-Viciana et al, 1994, 1996).

FIG. 3. (A) In vitro lipid substrate specificity of p110δ. GST-p110δ/p85α was used in a lipid kinase assay using the indicated substrates in the presence of $Mg^{2+}$. Equal cpm were spotted at the origin. (B) HPLC analysis of the PtdIns phosphorylation product generated by GST-p110δ/p85α. Elution times of the deacylated product of p110δ (solid line) and glycerophosphoinositol-3P and glycerophosphoinositol-4P standards (dotted lines) are shown. The positions of the AMP and ADP controls are indicated by arrows.

Figure 4A:
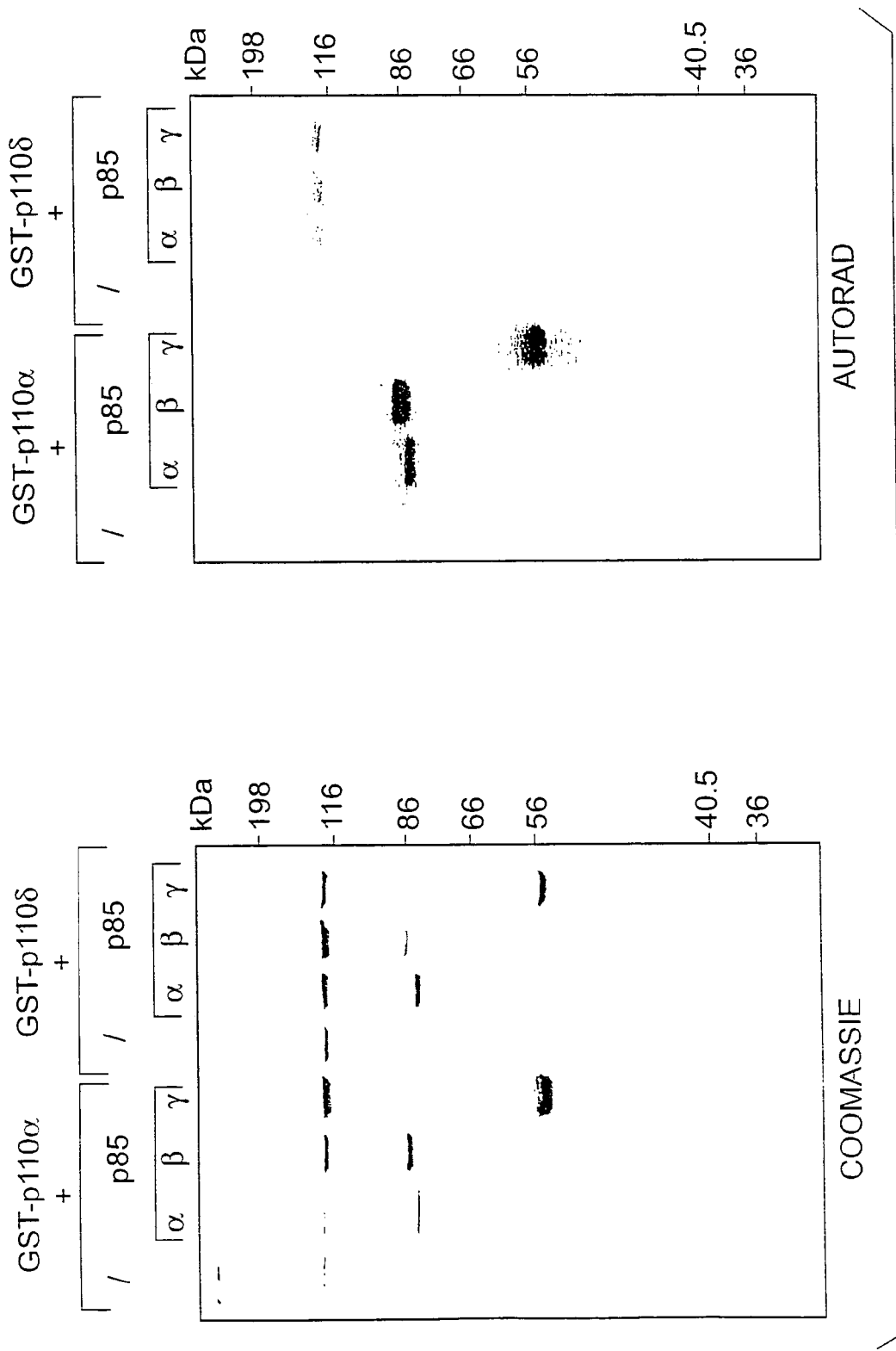

FIG. 4. Protein kinase activity of p110δ. (A) GST-p110α or GST-p110δ, in complex with the indicated p85 subunits, were subjected to an in vitro protein kinase reaction in the presence of $Mn^{2+}$, and further analysed by SDS-PAGE, Coomassie staining, and autoradiography, (B,C) Untagged p110α and p110δ [wild-type (WT) or kinase defective mutants (p110α-R916P and p110δ-R894P)], in complex with p85α or on PDGF-receptor phosphopeptide beads, were subjected to an in vitro kinase reaction and further analysed as described under (A). Open and closed arrowheads point to p110 and p85 proteins, respectively. Right panel in (B): phosphoamino acid analysis of p85α and p110δ.

FIG. 5. Sensitivity of p110δ lipid kinase activity to drugs. Inhibition of p110δ/p85α (closed circles) and p110α/p85α (open circles) is normalised to activity in the absence of the drug wortmannin. These data points are the mean (±SE) of 3 experiments.

Figure 6:
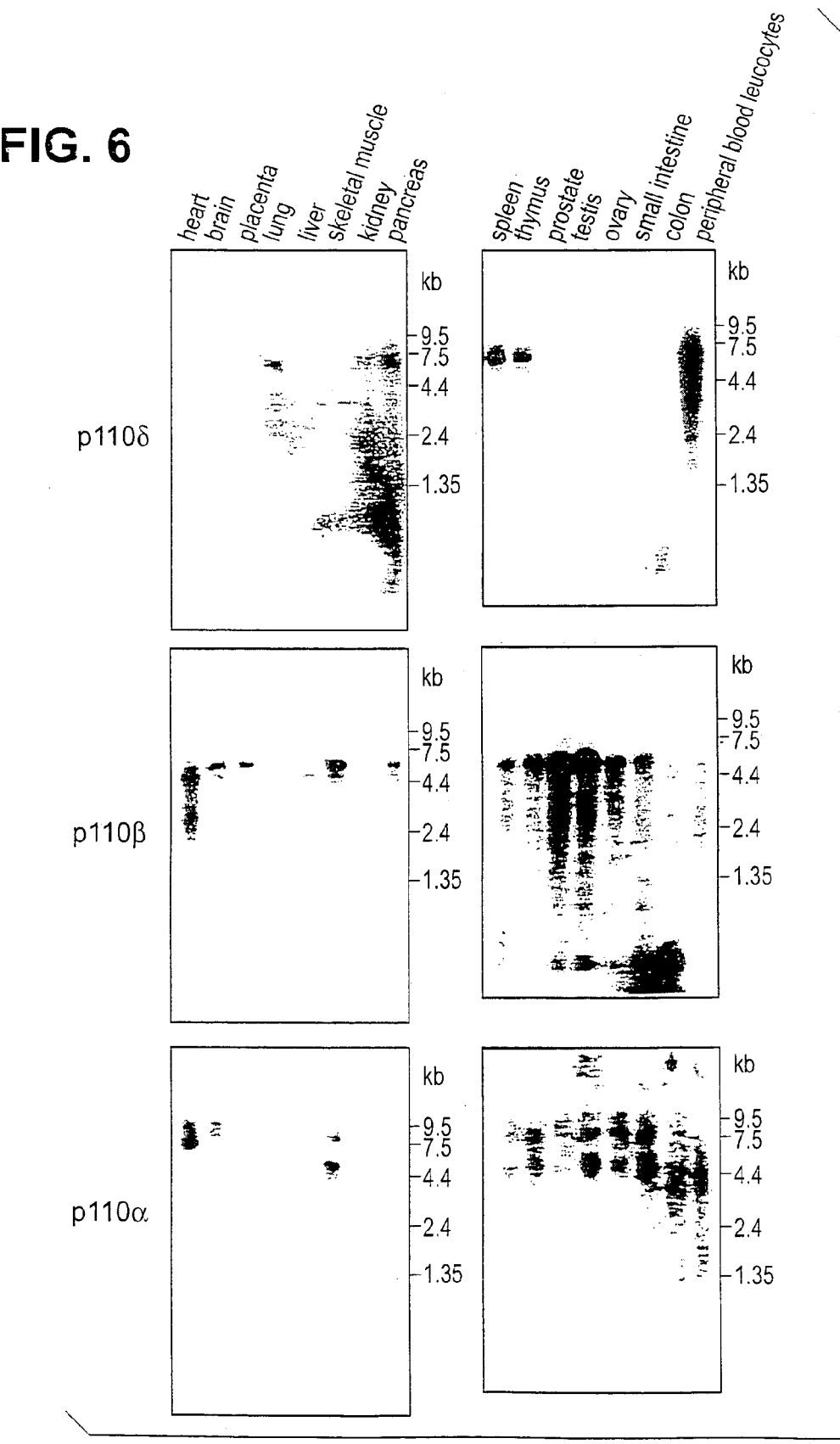

FIG. 6. Northern blot analysis of expression of p110α, p110β and p110δ.

Figure 7:
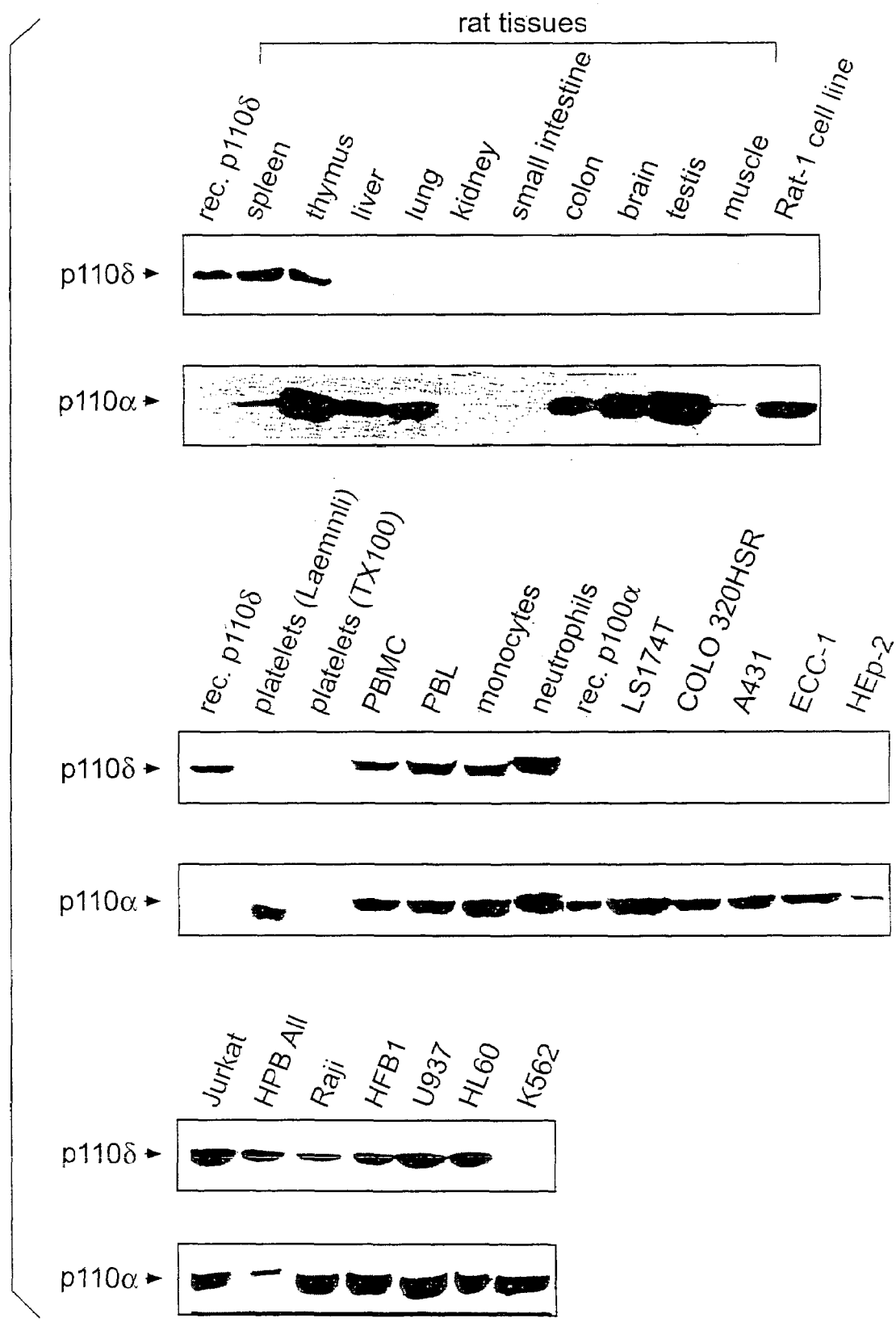

FIG. 7. Analysis of p110α and p110δ protein expression. 100 μg of total cell lysate was loaded per lane. Platelets were lysed in either lysis buffer as described under Materials and Methods, or in Laemmli gel loading buffer containing 2-mercaptoethanol. PMBC, peripheral blood mononuclear cells; PBL, peripheral blood lymphocytes.

Figure 8:
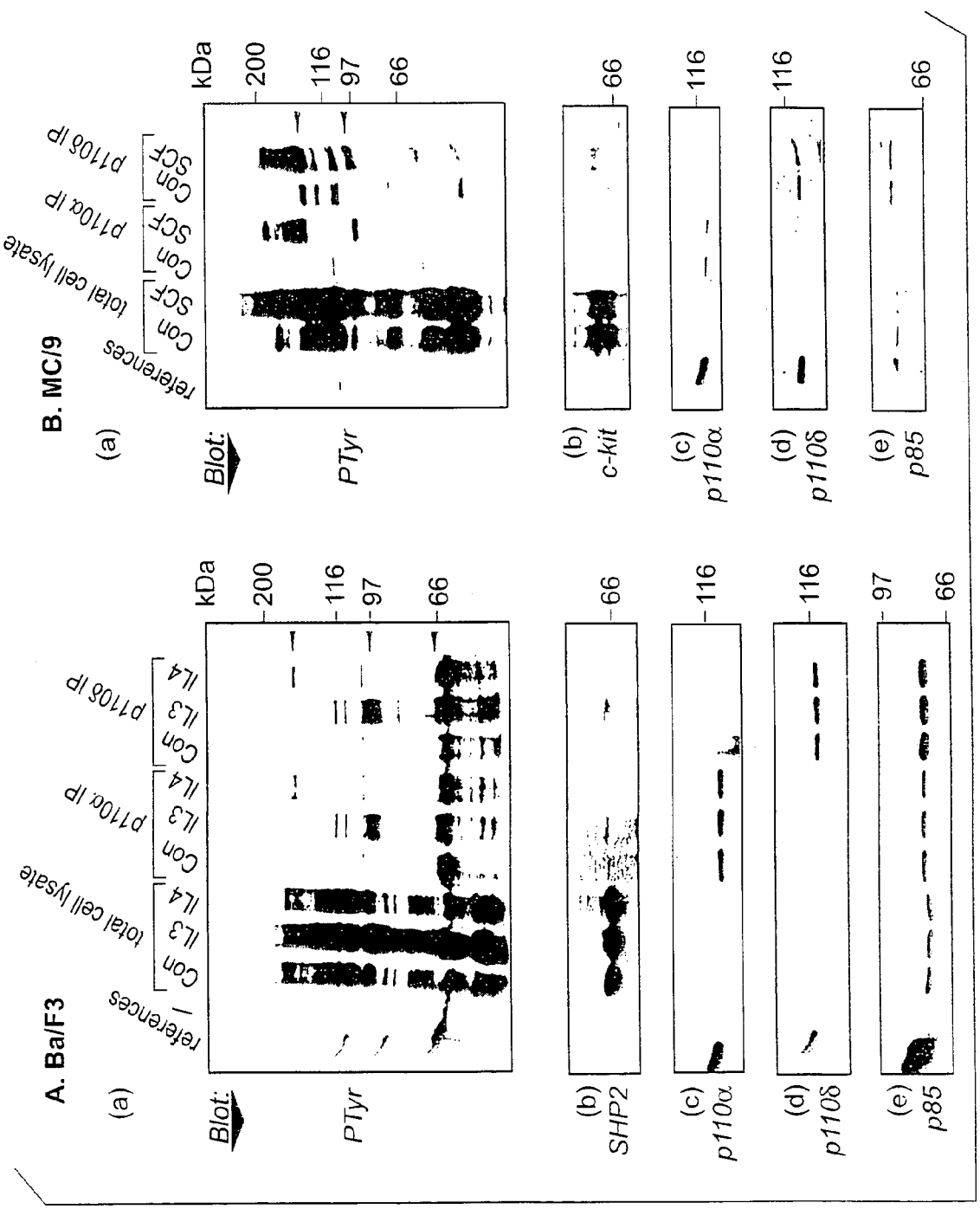

FIG. 8. Involvement of p110α and p110δ in cytokine signalling. Ba/F3 (A) and MC/9 (B) cell lines were stimulated with the indicated cytokines. Samples from control untreated cells are labelled Con. Total cell lysates, and p110α and p110δ IPs were separated by SDS-PAGE to prepare duplicate blots, the references for which were p110δ/85α (panels a, b and d) or p110α/85α (panels c and e). Immunoblotting of native blots were performed with 4G10 (anti-PTyr, panels a) and anti-p110α (panels c). Blots were subsequently stripped and reprobed with anti-SHP2. (A, panel b), anti-kit (B, panel b), anti-p110δ (panels d) and anti-p85 antibodies (panels e). The arrowheads indicate the positions of p170 (IRS-2), p100 and p70 (SHP2) (A, panel a), and of p150 (c-kit) and p110 (B, panel b).

FIG. 9. The complete human cDNA sequence of p110δ.

Figure 10:
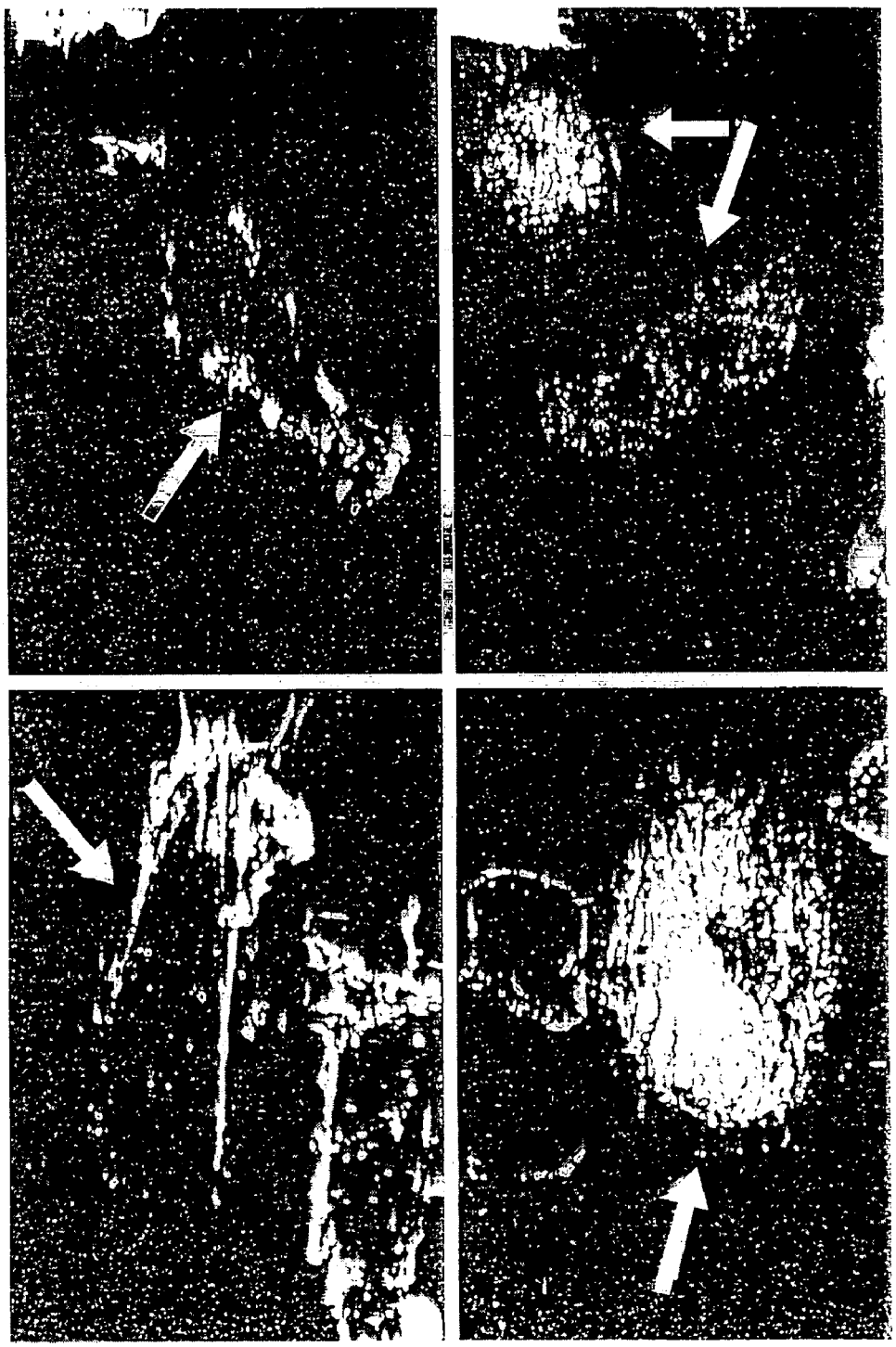

FIG. 10. Represents immunofluorescence images of murine macrophages microinjected with affinity purified antibodies to p110δ. The macrophage cytoskeletons are imaged with phalloidin conjugated rhodamine.

MATERIALS AND METHODS

Cloning of p110δ

Details of the isolation of partial PI3 kinase cDNA clones via RT-PCR based on homologous regions between bovine p110α and *S. cerevisiae* Vps34p have been described (Volinia et al., 1995: MacDougall et al., 1996). This approach yielded from the MOLT4 T cell line a partial p110δ cDNA fragment which was then used to screen an oligo(dT)-primed U937 cDNA library (Volinia et al., 1995). Complementary DNA was EcoRI-XhoI cloned in Lambda ZAPII vector digested with EcoRI-XhoI (Stratagene). Out of 4 million clones screened, 6 primary positive plaques were found, 3 of which remained positive during two further rounds of screening. The cDNA inserts in pBluescript were prepared by in vivo excision according to the manufacturer's (Stratagene) instructions. Three representative pBluescript clones ($0_{5.1}$, $0_{9.1}$, and $0_{11.1}$) were characterised by restriction mapping and PCR, and found to contain inserts with sizes ranging from 4.4 kb ($0_{11.1}$) to 5.0 kb $0_{5.1}$, $0_{9.1}$). Clone $0_{9.1}$ was used for detailed characterisation. Restriction mapping of its insert revealed the absence of an internal XhoI site, and the presence of 2 internal EcoRI sites, respectively 223 and 3862 nucleotides 3' from the EcoRI cDNA insertion site (nucleotide 1=underlined nucleotide of FIG. 9). Consequently, combined EcoRI and XhoI digest divided the $0_{9.1}$ insert in 3 fragments, further indicated as EcoRI fragment I (nucleotide 1-222), EcoRI fragment II (nucleotide 223-3861) and EcoRI-XhoI fragment III (nucleotide 3862-5000 approximately). Both strands of fragments I and II were sequenced using the Taq DyeDeoxy Terminator Cycle sequencing system (ABI) and the complete cDNA sequence is shown in FIG. 9. An open reading frame spanning nucleotides 195 to 3330 of the $0_{9.1}$ insert was found. An in frame stop codon precedes the potential start codon, which lies in a favourable context for translation initiation (Kozak, 1991). This results in 196 nucleotides of 5' untranslated region (UT) and approximately 2.2 kb 3' UT. In the sequenced 5' end of $0_{5.1}$, $0_{9.1}$ and $0_{11.1}$ clones, 2 different but related 5' untranslated regions were found indicative for the existence of at least 2 slightly different messenger RNAs.

Construction of Expression Vectors for p110δ

Insect cell transfer vectors used were pVL1393 (for untagged p110δ; InVitrogen) and pAcG3X (for GST-p110δ; Davies et al., 1993). The coding region for p110δ was subcloned in these vectors in two steps. First, the expression vectors were engineered, via linker insertion at the multicloning site, to contain part of the sequence of EcoRI fragment I of p110δ, spanning the start codon (at nucleotide 197; see above) to the second EcoRI site (nucleotide 223; see above). In the latter EcoRI site, EcoRI fragment II of p110δ was subcloned, followed by selection for clones with correctly orientated inserts. The first step for the insect cell vectors was BamHI-EcoRI cleavage followed by insertion of the following linker (linker I):

```
GATCCCCACCATGCCCCCTGGGGTGGACTGCCCCATGG (sense: 5'-3')

(antisense: 5'-3') AATTCCATGGGGCAGTCCACCCCAGGGGGCATGGTGGG
```

This linker contains the ATG with an optimal Kozak consensus sequence (Kozak, 1991). Further derivatives of p110δ were made by PCR using Vent DNA polymerase (New England Biolabs). P110δ EcoRI fragment II, subcloned in pBluescript-SK (further indicated as pBluescript-p110δ-EcoII) was hereby used as a template. In these PCR reactions, the 3'-untranslated region of the EcoRI fragment II insert was removed. Oligonucleotides used to create the mutation R894P were as follows: sense mutagenic oligonucleotide=PRIMER 1 (mutagenic residue underlined)

```
5'-GTGTGGCCACATATGTGCTGGGCATTGGCGATCCGCACAGCGACA
ACATCATGATCCG,

Anti-sense = PRIMER 2 =
5'-GGCCCGGTGCTCGAGAATTCTACTGCCTGTTGTCTTTGGACACGT
TGTGGGCC.
```

A parallel PCR was performed using primer 2, and a sense primer (PRIMER 3=5'-GTGTGGCCACATATGT-GCTGGGCATTGGCG) leaving the wild type p110δ sequence intact. All PCR products were cleaved with NdeI and XhoI, subcloned into NdeI-XhoI-opened pBluescript-p110δ-EcoII and sequenced. Correct clones were then transferred as an EcoRI cassette into EcoRI-opened pVL1393 containing linker I followed by selection for clones with correctly orientated insert.

Expression of p110δ in Insect Cells

Plasmid DNA was cotransfected with BaculoGold DNA (Pharmingen, San Diego, Calif.) using Lipofectin reagent (Gibco), Recombinant plaques were isolated and characterised by established methods (Summers and Smith, 1987).

Cell Culture

Cells were cultured in a humidified 5% $CO_2$ incubator in RPMI 1640 medium supplemented with 10% fetal bovine serum, 20 µM 2-mercaptoethanol, 100 units/ml penicillin/streptomycin and 2 µM glutamine. Ba/F3 is a murine IL3-dependent pre-B cell line (Palacios and Steinmetz, 1985) and MC/9 is a murine IL3-dependent mast cell line (Nabel et al., 1981). Both Ba/F3 and MC/9 were maintained in 10% (v/v) conditioned medium derived from WEHI3B, as the source of murine IL3. FDMAC11/4.6 (FD-6) myeloid progenitor cells are an indigenous variant of FDMAC11 which will grow in response to IL4, as well as IL3, GM-CSF and CSF-1 (Welham et al., 1994a). These cells were maintained in 3% (v/v) IL4-conditioned medium derived from the AgX63/OMIL4 cells (Karasuyama and Melchers, 1988).

Lipid Kinase Assay

Lipid kinase activity was performed essentially as described by Whitman et al. (1985). Lipid kinase assay buffer was 20 mM Tris HCl pH 7.4, 100 mM NaCl and 0.5 mM EGTA. Lipids were purchased from Sigma. The final concentration of ATP and $Mg^{2+}$ in the assay were routinely 0.5 and 3.5 mM, respectively, while lipids were used at 0.2-0.4 mM concentration. Unless otherwise indicated, kinase reaction was for 10 min at 37° C. The solvent for TLC separation of reaction products was propan-1-ol/2 M acetic acid/5 M $H_3PO_4$ (65:35:1). Assays of drug effects on the kinase were performed using PtdIns as substrate in the presence of 40 µM ATP (final) for 10 min at 25° C.; all tubes contained 1% DMSO. Activity was quantified by phosphorimager (Molecular Dynamics) analysis of TLC-separated lipid products.

HPLC Analysis

[$^{32}$P]-PtdIns3P, prepared by phosphorylating PtdIns with recombinant p110α, and [$^{32}$P]-PtdIns4P, generated by converting PtdIns with A431 membranes in the presence of 0.5% NP-40, were used as standards. Glycerophosphoinositols, generated by deacylation of lipids with methylamine (Clarke and Dawson, 1981), were separated by anion exchange HPLC on a PartisphereSAX column (Whatman International) using a linear gradient of 1 M $(NH_4)_2HPO_4$ against water (0-25% B; 60 min) at 1 ml/min. Radioactive peaks were detected by an on-line detector (Reeve Analytical, Glasgow). ADP and ATP nucleotide standards, added as internal controls to ensure consistency between runs, were detected by absorbance at 254 nm.

In Vitro Protein Phosphorylation Assay and Effect on Lipid Kinase Activity

Precipitated proteins were incubated for 30 min at 37° C. in protein kinase assay buffer (20 mM Tris.HCl (pH 7.4), 100 mM NaCl, 0.5 mM EGTA, 50 µM ATP and 1 mM $MnCl_2.4H_2O$, 5-10 µCi[γ-$^{32}$P]ATP/ml). The reaction was stopped by addition of SDS-PAGE sample buffer, and the reaction products analysed by SDS-PAGE and autoradiography. Phosphoamino acid analysis was performed on a Hunter thin layer electrophoresis system (CBS Scientific Co, Del Mar, Calif.) as described (Jelinek and Weber, 1993).

Interaction of Small GTP-Binding Proteins with PI-3K In Vitro

Binding of ras, rac and rho to GST-PI3K was performed as described (Rodriguez-Viciana et al., 1995, 1996).

Antibodies, Immunoprecipitations and Immunoblotting

Monoclonal antibodies to bovine p85α (U1, U13), and p85β (T15) have been described (End et al., Reif et al., 1993). A monoclonal antibody (I2) against bovine p85γ was developed in our laboratory. Rabbit polyclonal antiserum against GST-human p85α (AA 5-321) was kindly provided by Dr. P. Shepherd, University College London. Rabbit polyclonal antisera were raised against a C-terminal peptide of p110δ (C)KVNWLAHNVSKDNRQ$_{1044}$ and against an N-terminal peptide of human p110α (CGG)SVTQEAEEREEFFDE-TRR$_{88}$. To raise antibodies directed against the phosphorylated form of p110δ, the peptide sequence 1044 was phosphorylated at the serine residue during peptide synthesis. An antiserum to the C-terminus of human p110α (KMDWIFH-TIKQHALN) was kindly provided by Dr. Roya Hooshmand-Rad (Ludwig Institute for Cancer Research, Uppsala, Sweden). Antibodies were affinity-purified on peptides coupled to Actigel (Sterogene Bioseparations, Arcadia, Calif.) or to AF-Amino ToyoPearl TSK gel (Tosho Co, Japan). Antibodies were found to be specific for the PI3K to which they were directed (tested against the following panel of PI-3K, expressed in Sf9 cells: bovine p110α, human p110β (C. Panaretou and R. S.; unpublished results), human p110γ (Stoyanov et al., 1995), p110δ, PI-specific 3-kinase (Volinia et al., 1995). Peripheral blood cells were purified over a ficoll gradient (Lymphoprep; Nycomed, Oslo, Norway). Neutrophil cytosol was prepared by sonication as described (Wientjes et al., 1993). Lysis buffer was 1% Triton-X100, 150 mM NaCl, 1 mM EDTA, 1 mM NaF, 1 mM NaVO$_3$, 1 mM DTT, 1 mM PMSF, 0.27 TIU/ml aprotinin and 10 µM leupeptin. In some experiments, 1 mM disopropylfluorophosphate and 27 mM Na-p-tosyl-L-lysine chloromethyl ketone (hydrochloride) were added. Lysis buffer used for cytokine experiments was 50 mM Tris.HCl, pH 7.5, 10% (v/v) glycerol, 1% (v/v) NP-40, 150 mM NaCl, 100 µM sodium molybdate, 500 µM sodium fluoride, 100 µM sodium orthovanadate, 1 mM EDTA, 40 µg/ml PMSF, 10 µg/ml aprotinin, 10 µg/ml leupeptin, 0.7 µg/ml pepstatin, 1 mM DIFP, 1 mM TLCK). Cytokine-stimulated cells were pelleted and lysed at 2×10$^7$ cells/ml as described (Welham and Schrader, 1992) with the exception that lysates were clarified for 5 min in a microfuge ay 4° C. prior to further analyses. Immunoprecipitations were carried out as described (Welham et al., 1994a) PDGF-receptor peptide (YpVPMLG) was coupled to Actigel according to the manufacturer's instructions. C-terminal antiserum to p110δ was used for both immunoprecipitations and immunoblotting. For p110α, the C- and N-terminal antisera were used for immunoprecipitations and Westerns blot analysis, respectively.

SDS-PAGE and immunoblotting were carried out as described (Laemli, 1970; Welham and Schrader, 1992; Welham et al., 1994a). Antibodies were used at the following concentrations for immunoblotting: 4G10, antiphosphotyrosine monoclonal antibody at 0.1 µg/ml; anti-p110α and p110δ at 0.25 µg/ml; anti-p85 at 1:4000; anti-c-kit (Santa Cruz Biotechnology, sc-168) at 0.4 µg/ml, anti-SHP (Santa Cruz Biotechnology, sc-280) at 0.1 µg/ml and anti-IRS-2 (gift of Dr. M. White, Joslin Diabetes Center, Boston, Mass.) at 1:1000.

Both goat and anti-mouse and goat anti-rabbit horseradish peroxidase-conjugated antibodies (Dako, Denmark) were used at a concentration of 0.05 µg/ml. Immunoblots were developed using the ECL system (Amersham). Blots were stripped and reprobed as previously described (Welham et al., 1994a).

Injection of CSF-1 Stimulated Mouse Macrophages with Antibodies to p110δ and p110α

The murine macrophage cell-line, BAC1, was used in antibody micro injection experiments. The peptide polyclonal antibodies to p110δ were directed to either the C-terminal peptide 1044, (described p17 Materials and Methods), or to the peptide sequence (C)R222KKATVFRQPLVEQPED$_{238}$. Polyclonal sera were affinity purified before micro injection and were used at a concentration of 0.5-5 mg/ml. A control peptide polyclonal antisera to human P110α is as described on p17 of Materials and Methods. Before micro injection, Bac1 cells were starved of Colony Stimulating Factor 1 (CSF1) for 24 hours. Antibodies were then injected into CSF1 starved cells and exposed to CSF1 for 10-15 minutes before visualization of the cytoskeleton of micro injected Bac1 cells with phalloidin conjugated rhodamine, (preparation and visualisation of cells is as described in Allen et al 1997).

Cell Stimulations

Stimulation of cells with different growth factors was carried out as described (Welham and Schrader, 1992) with the exception that cells were resuspended at 2×10$^7$/ml in serum-free RPMI prior to stimulations. Chemically synthesized murine IL3 and IL4 were kindly provided by Dr. Ian Clark-Lewis (University of British Columbia, Vancouver). Recombinant murine SCF was purchased from R&D Systems Europe (Abingdon, Oxon). The concentration of growth factors and duration of stimulation (2 minutes for SCF; 10 minutes for IL3 and IL4) had been previously optimised to obtain maximal levels of tyrosine phosphorylation of receptors and cellular substrates. These were as follows, IL3 at 10 µg/ml (Welham and Schrader, 1992), IL4 at 10 µg/ml (Welham et al., 1994a) and SCF 50 ng/ml (M. J. W., unpublished observations).

Northern Blot Analysis

Northern blots of human polyA+ RNA (Clontech) were hybridized with random prime-labelled EcoRI fragment II of pBluescript clone 0$_{9.1}$. Stripping and reprobing using the following subsequent probes was then performed: internal EcoRI-XhoI 2.1 kb fragment from human p110α (Volinia et al., 1994) and EcoRI-XhoI 5 kb cDNA of human p110β (C. Panaretou; unpublished results).

Using the above described materials and methods we were able to elucidate data which describes the novel lipid kinase and in particular a PI3 Kinase which we have termed p110δ. Data relating to this kinase will now be described with a view to comparing p110δ with other members of the PI3 Kinase group so as to compare and contrast their respective characteristics.

Results

Cloning of p110δ

Degenerate primers based on conserved amino acid sequences (GDDLRQD and FHI/ADFG) in the kinase domain of bovine p110α and *S. cerevisiae* Vps34p were used in RT-PCR reactions with mRNA from the human MOLT4 T cell leukaemia. A partial cDNA, homologous but different from other known human PI3K, was obtained. This PCR fragment was used as a probe to screen a U937 monocyte library, and to isolate the corresponding full length clone (for details, see Materials and Methods and FIG. 9). Sequence analysis revealed a potential open reading frame, preceded by an in-frame stop codon. The potential start codon was also found to lie in a favourable context for translation initiation (Kozak, 1991). This open reading frame of 3135 nucleotides predicts a protein of 1044 amino acids with a calculated molecular mass of 119,471 daltons (FIG. 1A). Comparison of the amino acid sequence with other PI3K showed that this protein is most closely related to human p110β (58% overall identity; Hu et al., 1993), and more distantly to human p110α (41% identity; Volinia er al., 1994), human G-protein regulated p110γ (35% identity; Stoyanov et al., 1995) and the human vps34p analogue (28% identity; Volinia et al., 1995). The new PI3K described here will be further indicated as p110δ.

Figure 1C:
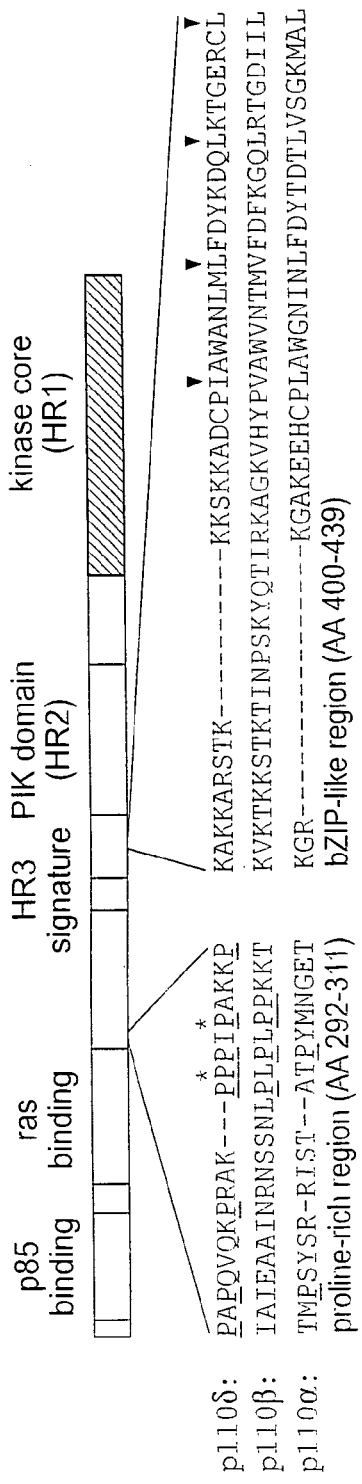

Dot plot comparison at high stringency (FIG. 1B) shows that p110α, β and δ are very homologous in the p85-binding region (AA 20-140 of p110α; Dhand et al., 1994) as well as in the C-terminal PI-kinase (PIK) domain (HR2) and catalytic core (AA 529-end of p110α, Zvelebil et al., 1996). An additional region of high sequence homology, spanning AA 370-470 of p110δ, was found in between the p85 binding site and HR2. This region contains the so-called HR3 signature (Wxx-LxxxIxIxDLPR/KxAxL) which is conserved in all p85-binding PI3Ks and in p110γ. The most N-terminal area of sequence difference between p110α and p110β/δ overlaps with the region defined in p110α as being sufficient for Ras binding (AA 133-314 in p110α; Rodriguez-Viciana et al., 1996). Two additional structural motifs were identified in p110δ. The first is a proline-rich region (FIG. 1B, C) for which molecular modelling indicates that it can form a left-handed, polyproline type-II helix with the potential to interact with SH3 domains (data not shown). In the corresponding region, p110α and p110β lack crucial prolines to allow a similar fold. The second motif is a basic-region, leucine-zipper (bZIP)-like domain, immediately C-terminal of HR3 (FIG. 1B, C). A bZIP region is present in both p110δ and p110β (and also in the Drosophila p110 (Leevers et al., 1997)), whereas the basic component of this domain is less prominent in p110α (FIG. 1C). Modelling of the p110δ ZIP region shows that its arrangement of L/V/I residues easily accommodates the formation of a helix structure which can form a coiled-coil dimeric protein zipper complex (data not shown).

p110δ Binds the p85 Adaptor and Ras Proteins

In order to verify the prediction from amino acid sequence comparison that p110δ might bind p85 subunits, p110δ was expressed in insect cells as a glutathione-S-transferase (GST)-fusion protein, together with recombinant baculoviruses encoding p85α, p85β or p85γ (the latter is a 55 kDa bovine p85 isoform homologous to p55$^{PIK}$, p55α and p85/AS53 (Pons et al., 1995; Inukai et al., 1996; Antonetti et al., 1996)). As is clear from FIG. 2A all p85 adaptor subtypes efficiently co-purified with GST-p110δ from co-infected cells.

Figure 2B:
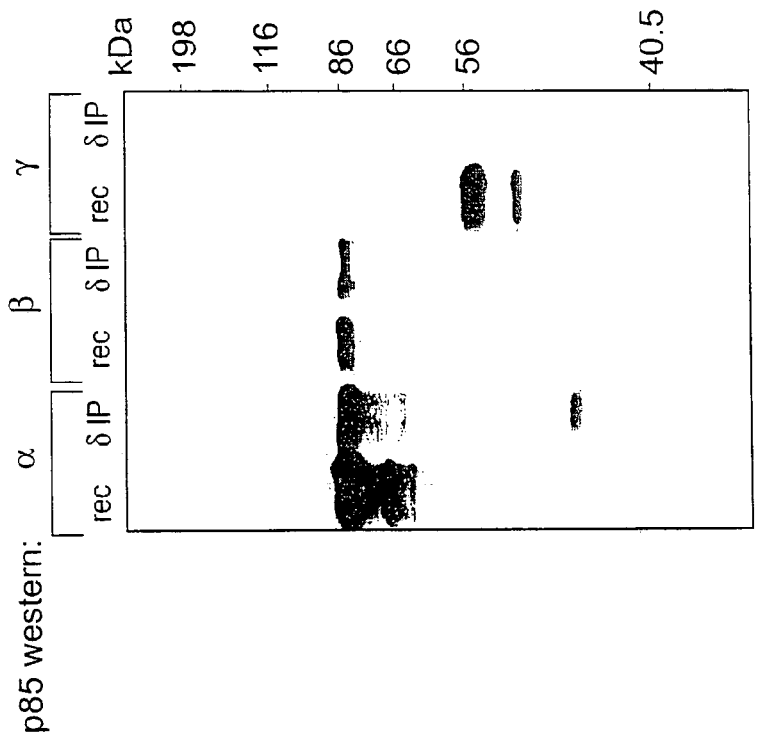
Figure 2A:
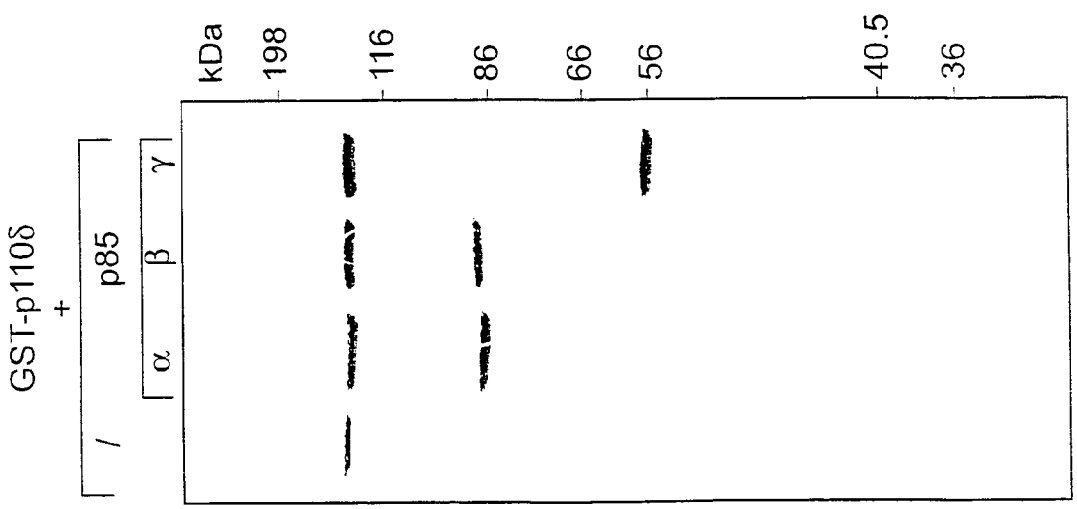

The question of whether different class I p110 catalytic subunits show binding preference for different p85 adaptor proteins in vivo has not been previously addressed. Using antiserum specific for p110δ, we found that both p85α and p85β were present in p110δ immunoprecipitates from different white blood cells (FIG. 2B shows the data for human neutrophils; note that p85γ is not expressed in leukocytes). Similar results were obtained for p110α (data not shown). In these immune complexes, a 45 kDa protein reactive with p85α antibodies was also observed (FIG. 2B). The nature of this protein is currently unclear, but it might be similar to a 45 kDa protein previously described to be present in p85 and p110 IPs from various tissues (Pons et al., 1995).

P110α and p110β have been shown to interact with Ras-GTP (Kodaki et al., 1995; Rodriguez-Viciana et al., 1994 and 1996). The region required for this interaction lies between AA 133 and 314 of these PI3Ks (Rodriguez-Viciana et al., 1996). Despite the relatively low sequence conservation with p110α and p110β in this region (FIG. 1C), certain apparently critical amino acids are conserved as p110δ does interact with Ras in vitro, in a GTP-dependent manner (FIG. 2C).

p110δ Binds ras, but Not rac or rho

Figure 2C:
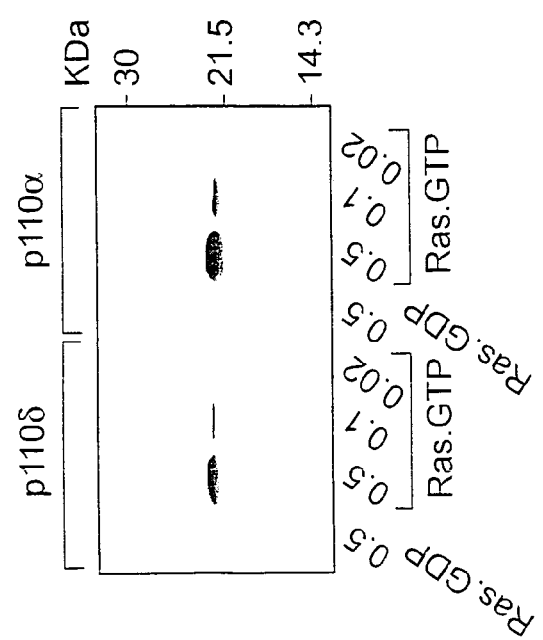

Incubation of GST-p110δ/p85α was found to retain GTP-bound wild-type ras or oncogenic V12-ras (FIG. 2C). This was not the case with GDP-loaded ras, or with A38-ras, a functionally dead ras mutant. Similar as for p110α, no binding of rho and rac could be demonstrated (data not shown).

Lipid Kinase Activity of p110δ

Figure 3A:
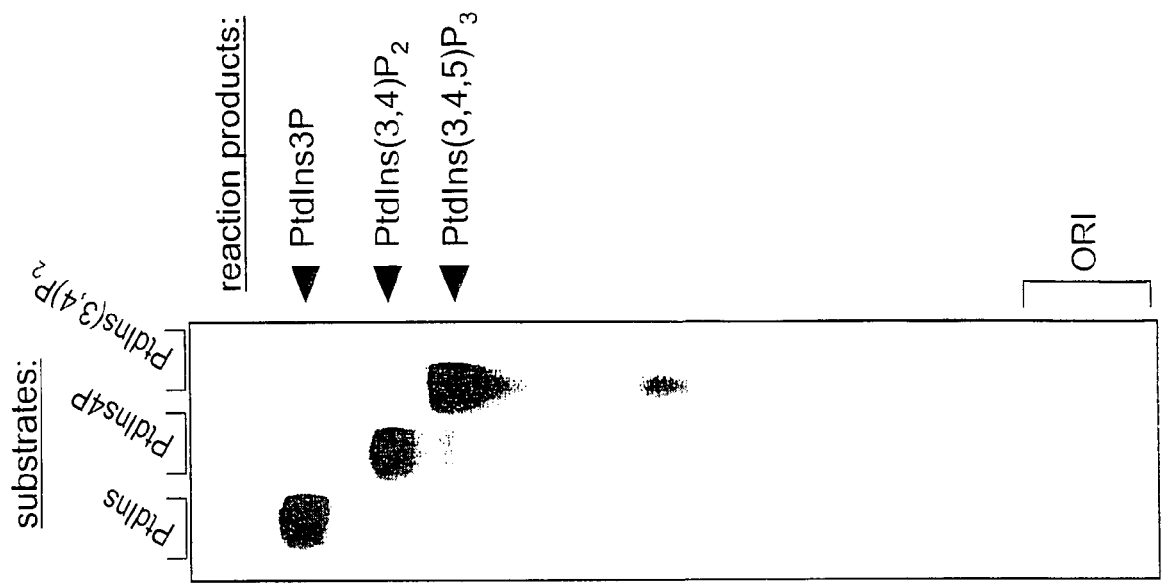
Figure 3B:
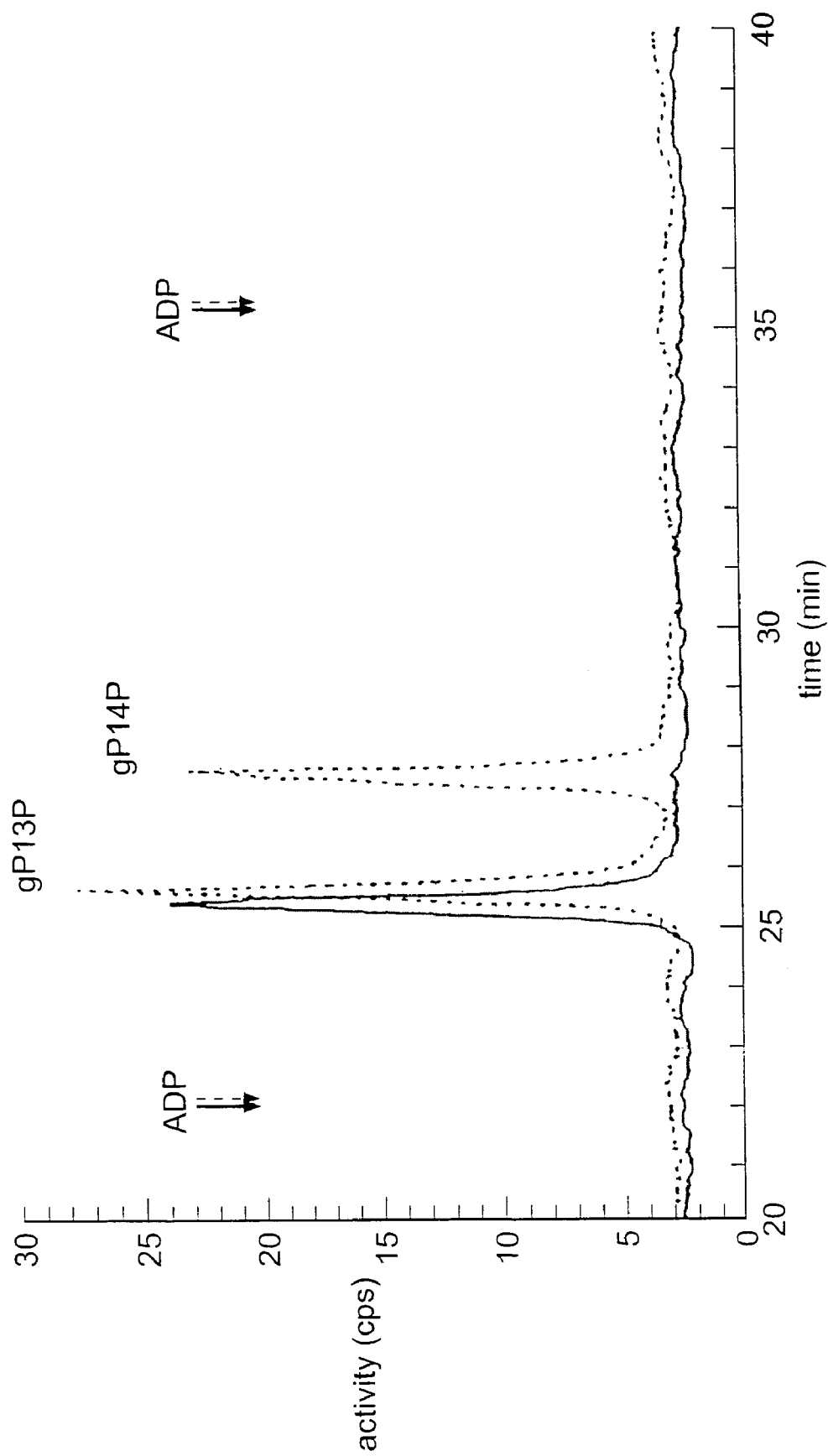

When tested in the presence of Mg$^{2+}$, p110δ was found to phosphorylate PtdIns, PtdIns4P and PtdIns(4,5)P$_2$ (FIG. 3A). HPLC analysis confirmed that these lipids are phosphorylated at the D3 position (FIG. 3B). Substrate preference in vitro was PtdIns >PtdIns4P>PtdIns(4,5)P$_2$ (data not shown). Lipid kinase activity was lower in the presence of Mn$^{2+}$ than in the presence of Mg$^{2+}$ (tested over the concentration range of 0.25 to 16 mM; data not shown). Specific activity of p110δ, isolated from Sf9 cells, was a factor 2-5 lower than that of p110α (data not shown). Taken together, these data establish p110δ as a genuine class I PI3K.

P110δ Does Not Phosphorylate p85 but Autophosphorylates.

Figure 4B:
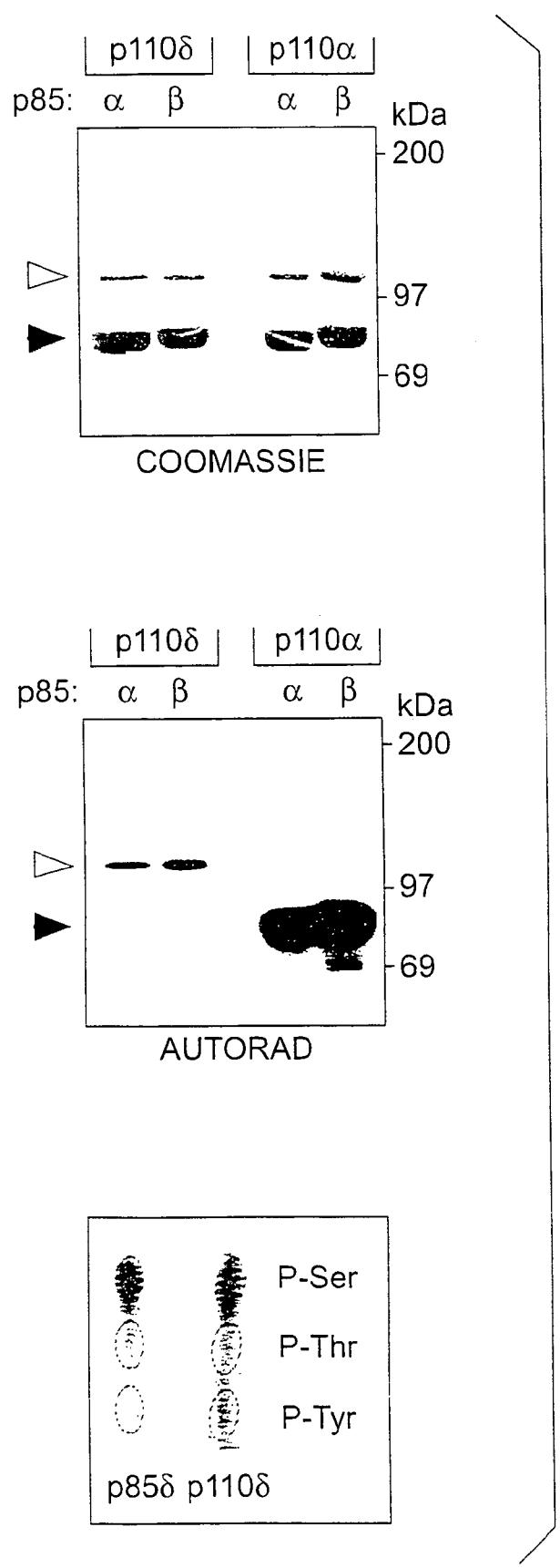
Figure 4C:
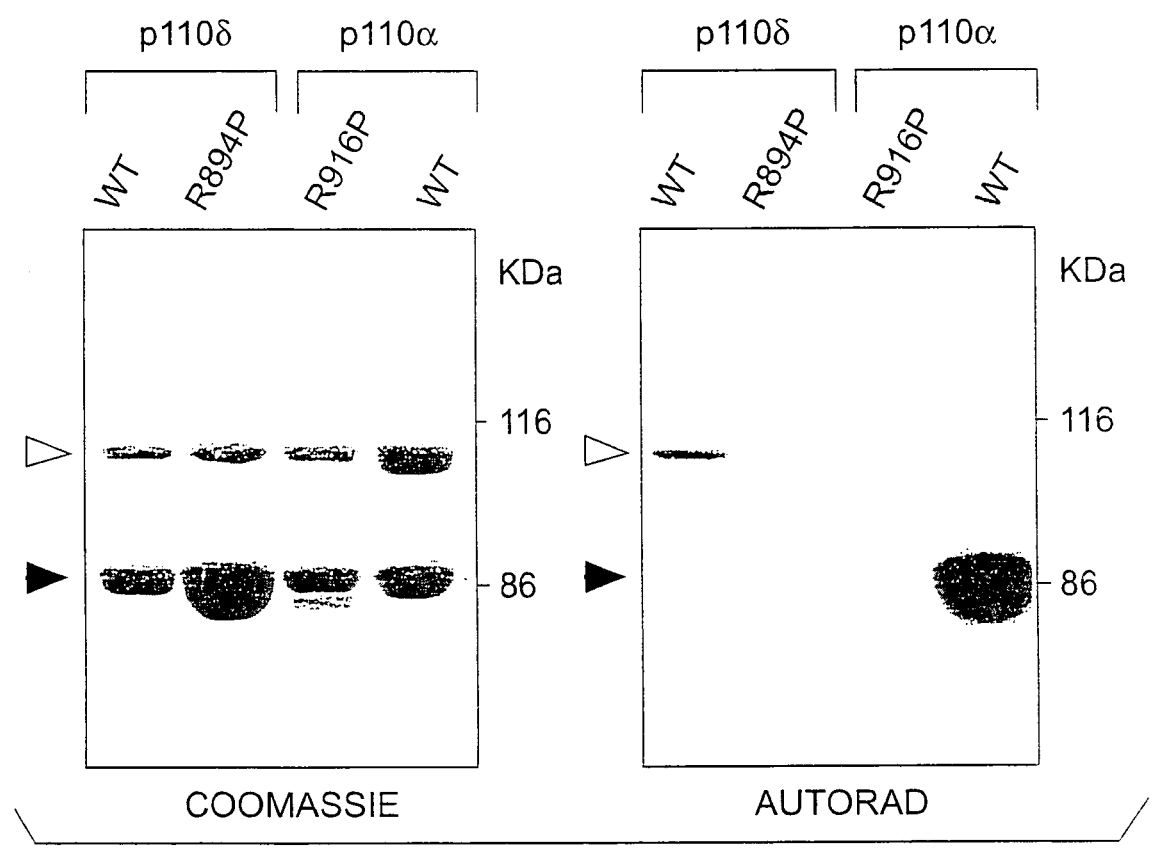

The p85 subunit has been demonstrated to be a substrate for a Mn$^{2+}$-dependent phosphorylation by the p110α catalytic subunit (Carpenter et al., 1993; Dhand et al., 1994). In contrast, GST-p110δ failed to phosphorylate coexpressed p85α, p85β or p85γ under a variety of in vitro conditions (partial data shown in FIG. 4A; no activity was seen either in the presence of Mg$^{2+}$ or Mn$^{2+}$). p85γ lacks an SH3 domain, and the absence of phosphorylation of this molecule by p110δ argues against the possibility that an intermolecular interaction of the p85α/β SH3 domain with the p110δ proline-rich region is locking up the p85 molecules for efficient phosphorylation by p110δ. In order to exclude that p110δ had already fully phosphorylated p85 during the in vivo co-expression in insect cells, exogenous purified p85α was added to immobilized GST-p110δ. After washing away the excess p85, bound p85 was found to be efficiently phosphorylated by p110α, but again not by p111δ (data not shown). When untagged p110δ, in complex with 85α or p85β, was subjected to an in vitro kinase assay in the presence of Mn$^{2+}$, p110δ autophosphorylated ((FIG. 4B note that this activity is largely absent in immobilised GST-p110δ (FIG. 4B)). Such phosphorylation was not seen in p110α/p85 complexes, in which again p85 was found to be phosphorylated (FIG. 4B). Phosphoamino acid analysis showed that the phosphorylation on p110δ occurred on serine (FIG. 4B). Both the phosphorylation of p85 by p110α and the autophosphorylation of p110δ were observed to be largely Mn$^{2+}$-dependent, with only very weak phosphorylation in the presence of Mg$^{2+}$ (data not shown). Autophosphorylation of p110δ resulted in reduced lipid kinase activity.

In order to exclude the possiblity that the observed phosphorylation of p110δ was due to a coprecipitated protein kinase, a kinase-defective p110δ mutant was generated. This was done by converting arginine 894 to proline in p110δ, generating p110δ-R894P. The mutated arginine residue is located in the conserved D$\underline{R}$X$_3$NX$_{12-13}$DFG motif of the kinase domain, likely to be part of the catalytic loop as in protein kinases (Taylor et al., 1992, Zvelebil et al., 1996). A similar mutation in bovine p110α (R916P) has been found to completely knock out catalytic activity (Dhand et al., 1994). As is clear from FIG. 4C, p110δ-R894P, expressed in insect cells, was no longer phosphorylated in precipitates of p110δ, indicating that the latter has indeed autophosphorylation capacity. Likewise, lipid kinase activity was found to be lost by p110δ-R894P (data not shown).

We have produced polyclonal antisera to the phosphorylated form of p110δ. The C-terminal peptide sequence 1044 was phosphorylated at the serine residue 1033 and used to immunize rabbits. The antisera directed against the phosphorylated peptide has enabled us to establish that p110δ is phosphorylated in vivo and upon cytokine stimulation this phosphorylation is enhanced (results not shown).

Drug Sensitivity of p110δ Catalytic Activity p110α and δ lipid kinase activity were found to exhibit a similar sensitivity to inhibition by wortmannin and LY294002 (FIG. 5), with an IC$_{50}$ of 5 nM (for wortmannin) and 0.5 µM (for LY294002). Likewise, the autophosphorylation activity of p110δ was also inhibited by wortmannin in the nanomalar range (data not shown)

Tissue Distribution of p110δ

The expression pattern of p110δ was investigated by Northern blot analysis of polyA$^+$ RNA of human tissues, and compared with that of p110α and p110β. A single messenger mRNA species of approximately 6 kb was found to be particularly highly expressed in white blood cell populations i.e. spleen, thymus and especially peripheral blood leucocytes (the latter contains all white blood cells with only the majority of the erythrocytes being removed) (FIG. 6). In some Northern blot experiments, an additional ~5 kb messenger for p110δ was also observed (data not shown). Low levels of p110δ messenger RNA expression were found in most other tissues examined, although it is difficult to exclude the possibility that blood cell contamination is responsible for this p110δ mRNA signal. p110α and p110β were also found to be expressed in most tissues examined (FIG. 6).

Antibodies specific for p110α and δ were then used to assay the expression of these PI3K at the protein level. Upon testing different rat tissues, a 110 kDa protein reactive with p110δ antibodies was found in spleen and thymus, but not in any of the other tissues tested (FIG. 7). This pattern largely confirms the data of the Northern blot analysis described above. p110δ was also found to be present in both primary and transformed white blood cells, independent of their differentiation stage (FIG. 7). In the primary blood cells, both the lymphoid and myeloid cell populations were positive for p110δ whereas platelets were not (FIG. 7). Both T (e.g. Jurkat, HPB All) and B (e.g. Raji, HFB1) cell lines expressed p110δ (FIG. 7). The 110 kDa p110δ was not found in Rat-1, NIH 3T3 and Swiss 3T3 fibroblasts, LS174T and COLO 320HSR colon adenocarcinomas, A431 epidermoid carcinoma, ECC-1 endometrial carcinoma and HEp-2 larynx carcinoma (FIG. 7) nor in CHO chinese hamster ovary, POC small-cell lung cancer cell line, porcine and bovine aortic endothelial cells, MDA-MB-468 breast adenocarcinoma, and primary human muscle and fibroblasts (data not shown). In conclusion, it appears that p110δ is selectively expressed in leukocytes.

In contrast to p110δ, p110α was found in most of the tissues and cell lines investigated, including the white blood cells (FIG. 7).

Micro Injection of Anti p110δ Polyclonal Antibodies Into CSF-1 Stimulated Murine Macrophages The possible function of p110δ was investigated further by a series of micro injection experiments of the murine macrophage cell-line, Bac1 with antisera to p110δ and p110α. Prior to micro injection, Bac1 cells were deprived of CSF1 for 24 hours. CSF1 deprivation primes cells to divide and become motile when subsequently exposed to CSF1. Affinity purified anti p110δ polyclonal antibodies were micro injected into CSF1 deprived Bac1 cells followed by exposure to CSF1 for 10-15 minutes.

The micro injected Bac1 cells show marked alterations in cellular morphology. The normal cell membrane ruffling disappears and cytoplasmic retraction occurs. The cytoskeleton of micro injected Bac1 cells was visualised using a phalloidin-rhodamine conjugate and FIG. 10 shows a representative sample of such cells showing a disorganised cytoskeletal arrangement. The injection of anti p110α does not produce an equivalent effect.

Interestingly a similar phenotype is shown by expression of the dominant-negative small GTP-binding protein rac, N17RAC. This suggests that p110δ may be part of the same signalling cascade that may be involved in cytoskeletal organisation and cellular motility.

p110δ is Involved in Cytokine Signalling

In leucocytes, p85-binding PI3Ks have been implicated in a wide variety of signalling events including signaling via cytokine and complement receptors, integrins, Fc receptors, B and T cell antigen receptors and their accessory molecules such as CD28 (reviewed by Stephens et al., 1993; Fry, 1994). Therefore, it is clear that a multitude of signalling processes could be potentially linked to p110δ. A crucial question is whether selective coupling of p110δ to the above-mentioned signalling/receptor complexes occurs in cells that also contain other class I PI3K, given the observation that different p110s seem to be complexed with the same p85 isoforms (FIG. 2B). We addressed this important question in the context of cytokine signal transduction, operative in diverse types of leukocytes.

Different families of cytokines transduce signals via discrete classes of receptors that share common gp130, β or γ chains, or via receptors with intrinsic tyrosine kinase activity (reviewed in Taga and Kishimoto, 1995). Whereas PI3K activation by cytokines signalling via gp130 has not been reported, activation of p85-binding PI3K in response to cytokine signalling via the common β chain (eg IL3), common γ chain (eg IL4), or via tyrosine kinase receptors (such as c-kit, which binds Stem Cell Factor (SCF)) has been demonstrated (Wang et al, 1992; Gold et al, 1994). We examined the ability of IL3, IL4 and SCF to couple to p110δ and p110α in cytokine-dependent leukocyte cell lines. An identical pattern of phosphotyrosine-containing proteins, specific to the cytokine used for stimulation, was found to co-precipitate with p110α and p110δ antibodies (FIG. 8, panel a). In the IL3- and IL4-responsive Ba/F3 pre-B and myeloid progenitor FD-6 cell lines (FIG. 8A; data for FD-6 are not shown), IL3-treatment induced the appearance in p110α/δ IPs of an unknown protein of 100 kDa and the 70 kDa protein tyrosine phosphatase, SHP2 (FIG. 8A, panel b). The 170 kDa protein co-precipitated upon IL4 stimulation (FIG. 8A, panel a) was shown by immunoblotting to be IRS-2, the major substrate of IL4-induced phosphorylation in these cells (data not shown). FIG. 8B shows the results of similar analyses in MC/9 mast cells. Following SCF stimulation, both p110α and p110δ IPs contained an unidentified 100 kDa tyrosine-phosphorylated protein as well as a 150 kDa protein identified as c-kit, the SCF receptor (FIG. 8B, panels a and b). Taken together, these data indicate that p110α and p110δ show no apparent differences in their recruitment to a variety of activated cytokine receptor complexes. In addition, the implication in cytokine signalling of at least two members of the p85-binding PI3K class reveals a previously unrecognised complication of signal transduction pathways downstream of these cytokine receptors.

Expression of PI3 Kinase p110 Sub Units in Murine and Human Melanoma Cell-Lines.

The expression of p110δ was further investigated in various murine and human melanoma cell-lines. A characteristic feature of a melanoma is the aggressive nature of the metastasis associated with this cancer. The possible involvement of p110δ in metastasis was investigated by analysing the relative abundance of p110δ protein in a range of murine and human cell-lines. Western blots were used to assess the levels of p110α and β as well as p110δ. J774, a murine cell-line, was used as a positive control for the murine western blots. Neonatal melanocytes were used as a control for the human western blot. Table 1 indicates that p110α and β are constitutively expressed in both control and melanoma cell-lines of both murine and human origin. Interestingly, the murine control cell-line J744 shows markedly reduced levels of p110δ when compared to the murine melanoma cell-lines.

However detectable levels of p110δ are found in human neonatal melanocytes. This may be explained by the nature of these human control cells. The expression of p110δ in these control cells may be explained by the relatively recent migration of these cells in the human skin and therefore residual levels of p110δ may be present in these cells. Adult melanocytes have prolonged residence in skin and the level of p110δ may be reduced to undetectable levels commensurate with their terminal differentiation.

We have described a novel human p110 subunit, p110δ, which is part of the PI3 kinase family. p110δ shows a restricted expression pattern, only accumulating to significant levels in white blood cells populations and particularly in peripheral blood leucocytes. The motile nature of these cells has lead us to propose that this member of the PI3 kinase family may be involved in regulating the motility of cells via cytoskeletal reorganisation. The data relating to murine and human melanoma cell lines is interesting but inconclusive with regard to human melanomas. The use of tissue biopsies of normal human melanocytes and human melanomas will allow this to be resolved.

TABLE 1

| Cell-line | Characteristic | δ | α | β | Reference |
|---|---|---|---|---|---|
| Expression of p110 Subunits in Murine Melanomas | | | | | |
| Murine | | | | | |
| J774 | Control | − | + | + | This study |
| Melan-c | Melanoma | − | + | + | |
| Melan-pl | Melanoma | − | + | + | Wilson et al 1989 |
| Melan-a Tu-2d | Melanoma | − | + | + | Wilson et al 1989 |
| Mel-ab | Melanoma | +/− | + | + | Dooley et al 1988 |
| Mel-ab-LTR-Ras2 | Melanoma | + | + | + | Dooley et al 1988 |
| Mel-ab-LTR Ras 3 | Melanoma | + | + | + | Dooley et al 1988 |
| Mel-ab-pMT | Melanoma | + | + | + | Dooley et al 1988 |
| B16 F1 | Melanoma (weakly metastatic) | + | + | + | Fidler et al 1975 |
| B16 F10 | Melanoma (highly metastatic) | + | + | + | Fidler et al 1975 |
| Expression of p110 Subunits in Human Melanomas | | | | | |
| Human | | | | | |
| A375P | Melanoma (weakly metastatic) | − | + | + | Easty et al 1995 |
| A375M | Melanoma (highly metastatic) | + | + | + | Easty et al 1995 |
| WM164 | Melanoma | + | + | + | Easty et al 1995 |
| WM451 | Melanoma | + | + | + | Easty et al 1995 |
| DX3 | Melanoma (weakly metastatic) | + | + | + | Ormerod et al 1986 |
| DX3-LT5.1 | Melanoma (Highly metastatic) | − | + | + | Ormerod et al 1986 |
| Control (human neonatal melanocytes) | Primary cells | + | + | + | This study |

REFERENCES

Antonetti, D. A., Algenstaedt, P. and Kahn, C. R. (1996) Insulin receptor substrate 1 binds two novel splice variants of the regulatory subunit of phosphatidylinositol 3-kinase in muscle and brain. *Mol. Cell. Biol.*, 16, 2195-2203.

Burgering, B. M. T. and Coffer, P. J. (1995) Protein kinase B (c-Akt) in phosphatidylinositol-3-OH kinase signal transduction. *Nature*, 376, 599-602.

Carpenter, C. C., Auger, K. R., Duckworth, B. C., Hou, W.-M., Schaffhausen, B. and Cantley, L. C. (1993) A tightly associated serine/threonine protein kinase regulates phosphoinositide 3-kinase activity. *Mol. Cell. Biol.*, 13, 1657-1665.

Chung, J. K., Grammer, T. C., Lemon, K. P., Kazlauskas, A. and Blenis, J. (1994) PDGF- and insulin-dependent pp70$^{SK6}$ activation mediated by phosphatidylinositol-3-OH-kinase. *Nature*, 370, 71-75.

Clarke, N. G. and Dawson R. M. C. (1981) Alkaline O->N-transacylation. A new method for the quantitative deacylation of phosphlipids. *Biochem. J.*, 195, 301-306.

Cross, D. A. E., Alessi, D. R. Cohen, P., Andjelkovich, M. and Hemmings, B. A. (1995) Inhibition of glycogen synthase kinase-3 by insulin mediated by protein kinase B. *Nature*, 378, 785-789.

Davies, A. H., Jowett, J. B. M. and Jones, I. A. (1993) Recombinant baculovirus vectors expressing glutathione-S-transferase fusions proteins. *Biotechnology*, 11. 933-936.

DeCamilli, P., Emr, S. D., McPherson, P. S. and Novick, P. (1996) Phosphoinositides as regulators in membrane traffic. *Science*, 271, 1533-1539.

Devereux, J., Haeberli, P. and Smithies, O. (1984) A comprehensive set of sequence analysis programsforthe VAX. *Nucleic Acids Res.*, 12, 3897-395.

Dhand, R., Hiles, I., Panayotou, G., Roche, S., Fry, M. J., Totty, N. F., Truong, O., Vicendo, P., Yonezawa, K., Kasuga, M. M., Courtneidge, S. and Waterfield, M. D. (1994) PI 3-kinase is a dual specificity enzyme: autoregulation by an intrinsic protein-serine kinase activity. *EMBO J.*, 13, 522-533.

Divecha, N. and Irvine, R. F. (1995) Phospholipid signaling. *Cell*, 80, 269-278.

Dooley et al., (1988). Oncogene, 3, p531.

Easty et al., (1995). Int. J. Cancer, 60, 129-136.

End, P., Gout, I., Fry, M. J., Panayotou, G., Dhand, R., Yonezawa, K., Kasuga, M. and Waterfield, M. D. (1993). A biosensor approach to probe the structure and function of the p85α subunit of the phosphatidylinositol 3-kinase complex, *J. Biol. Chem.*, 268, 10066-10075.

Fidler, I. (1975). Cancer Research, 35, 218-224.

Franke, T. F., Yang, S. I., Chan T. O., Dataa, K., Kazlauskas, A., Morrison, D. K., Kaplan, D. R. and Tsichlis, P. N. (1995) The protein kinase encoded by the Akt proto-oncogene is a target of the PDGF-activated phosphatidylinositol 3-kinase. *Cell*, 81, 727-736.

Fry, M. (1994) Structure, regulation and function of phosphoinositide 3-kinases. *Biochim. Biophys. Acta.* 1226, 237-268.

Gold, M. R., Duronio, V., Saxena, S. P., Schrade, J. W. and Aebersold, R. (1994) Multiple cytokines activate phosphatidylinositol 3-kinase in hemopoietic cells. Association of the enzyme with various tyrosine-phosphorylated proteins. *J. Biol. Chem.*, 269, 5403-5412.

Gout, I., Dhand, R., Hiles, I. D., Fry, M. J., Panayotou, G., Das, P., Truong, O., Totty, N. F., Hsuan, J., Booker, G. W., Campbell, I. D. and Waterfield, M. D. (1993) The GTPase dynamin binds to and is activated by a subset of SH3 domains. *Cell*. 75, 1-20.

Hartley, D., Mleisner, H. and Corvera, S. (1995) Specific association of the βisoform of the p85 subunit of phosphatidylinositol-3 kinase with the proto-oncogene c-cbl. *J. Biol. Chem.*, 270, 18260-18263.

Hawkins, P. T., Eguinoa, A., Giu, R.-G., Stokoe, D., Cooke, F. T., Walters, R., Wennström, S., Claesson-Welsh, L., Evans, T., Symons, M. and Stephens, L. (1995) PDGF stimulates an increase in GTP-Rac via activation of phosphoinositide 3-kinase. *Curr. Biol.*, 5, 393-403.

Hiles, I. D., Otsu, M., Volinia, S., Fry, M. J., Gout, I., Dhand, R., Panayotou, G., Ruiz-Larrea. F., Thompson, A., Totty, N. F., Hsuan, J. J., Courtneidge, S. A., Parker, P. J. and Waterfield, M. (1992) Phosphatidylinositol 3-kinase: structure and expression of the 100 kd catalytic subunit. *Cell,* 419-429.

Hirai, S., Izawa, M., Osada, S., Spyrou, G. and Ohno S. (1996) Activation of the JNK pathway by distantly related protein kinases, MEKK and MUK. *Oncogene,* 12, 641-650.

Hu, P., Mondino, A., Skoinik, E. Y. and Schiessinger, J. (1993) Cloning of a novel ubiquitously expressed phosphatidylinositol 3-kinase and identification of its binding site on p85. *Mol. Cell. Biol.* 13, 7677-7688.

Hunter, T. (1995) When is a lipid kinase not a lipid kinase? When it is a protein kinase. *Cell.* 83, 1-4.

Ing, Y. L., Lewung, I. W., Heng, H. H., Tsui, L.-C. and Lassam, N. J. (1994) MLK-3: identification of a widely-expressed protein kinase bearing an SH3 domain and a leucine zipper-basic region domain. *Oncogene,* 9, 1745-1750.

Inukai, K., Anai, M., Van Breda, E., Hosaka, R., Katagiri, H., Funaki, M., Fukushima, Y., Ogihara, T., Yazaki, Y., Kikuchi, M., Oka, Y. and Asano, Y. (1996) A novel 55-kDa regulatory subunit for phosphatidylinositol 3-kinase structurally similar to p55PIK is generated by alternative splicing of the p85α gene. *J. Biol. Chem.,* 271, 5317-5320.

James, S. R., Downes, C. P., Gigg, R., Grove, S. J. A., Holme, A. B. and Alessi, D. (1996) Specific binding of the Akt-1 protein kinase to phosphatidylinositol 3,4,5-triphosphate without subsequent activation. *Biochem. J.,* 315, 709-713.

Jelinke, T. and Weber, M. J. (1993) Optimization of the resolution of phosphoamino acids by one-dirnensional thin-layer electrophoresis. *Biotechniques.* 15, 628-630.

Kapeller, R. and Cantley, L. C. (1994) Phosphatidylinositol 3-kinase. *BioEssays,* 8, 565-576.

Karasuyama, H. and Melchers, F. (1988) Establishment of mouse cell lines which constitutively secrete large quantities of interleukin 2, 3, 4 or 5, using modified cDNA expression vectors. *Eur. J. Immunol.,* 18, 97-104.

Klippel, A., Reinhard, C., Kavanaugh. W. M., Apell, G., Escobedo, M.-A. and Williams, L. T. (1996) Membrane localization of phosphatidylinositol 3-kinase is sufficient to activate multiple signal-transducing kinase pathways. *Mol. Cell. Biol.* 16, 4117-4127.

Koadki, T., Woscholski, R., Hallberg, B., Rodriguez-Viciana, R., Downward, J. and Parker, P. J. (1994). The activation of phosphatidylinositol 3-kinase by Ras. *Curr. Biol.,* 4, 798-806.

Kozak, M. (1991) Structural features in eukaryotic mRNAs that modulate the initiation of translation. *J. Biol. Chem.,* 266, 19867-19870.

Laemmli, U. K. (197) Cleavage of structural proteins during the assembly of the head of bacteriophasge T. *Nature* 227, 680-685.

Lam, K., Carpenter. C. L., Ruderman, N. B., Friel. J. C. and Kelly, K. L. (1994) The phosphatidylinositol 3-kinase serine kinase phosphorylates IRS-1. *J. Biol. Chem.,* 269, 24648-20652.

Leevers, S. J., Weinkove, D., MacDougall, L. K., Hafen, E. and Waterfield, M. D. (1997) The *Drosophilla* phosphoinositide 3-kinase Dp110 promotes cell growth. *EMBO. J.* In press.

Li, G., D'Souza-Schorey, C., Barbieri, M. A., Roberts, R. L., Klippel, A., Williams, L. T. and Stahl, P. D. (1995) Evidence for phosphatidylinositol 3-kinase as a regulator of endocytosis via activation of Rab5. *Proc. Natl. Acad. Sci. USA.* 92. 10207-12211.

MacDougall, L. K., Domin, J. and Waterfield, M. D., (1996) A family of phosphoinositide 3-kinases in *Drosophila* identifies a new mediator of signal transduction. *Curr. Biol.,* 5, 1404-1415.

Molz, L., Chen, Y.-W., Hirano, M. and Williams, L. T. 91996) Cpk is a novel class of *Drosophila* PtdIns 3-kinase containing a C2 domain. *J. Biol. Chem,* 271, 13892-13899.

Nabel, G., Gali, S. J., Dvorak, A. M., Dvorak, H. F. and Cantor, H. (1981) Inducer T lymphocytes synthesize a factor that stimulates proliferation of clones mast cells. *Nature.* 291, 332-334.

Ormerod et al., (1986). Cancer Research, 46, 884-890.

Otsu, M. Hiles, I., Gout, I., Fry, M. J., Ruiz-Larrea, F., Panayotou, G., Thompson, A. Dhand, R., Hsuan, J., Totty, N., Smith, A. D., Morgan, S., Courtneidge, S. Parker, P. J. and Waterfield, M. D. (1991) Characterization of two 85 kd proteins that associate with receptor tyrosine kinases, middle-T/pp60$^{c\text{-}src}$ complexes, and PI3-kinase. *Cell.* 65, 91-104.

Palacios, R. and Steinmetz, M. (1985) IL-3-dependent mouse clones that express B-220 surface antigen, contain Ig genes in germ-line configuration and venerate B lymphocytes in vivo. *Cell.* 41, 727-734.

Palmer, R. H., Dekker, L. V., Woscholski, R., Le Good, A., Gigg, R. and Parker, P. J. (1995) Activation of PRK1 by phosphatidyinositol 4,5-bisphosphate and phosphatidylinositol 3,4,5-trisphosphate. *J. Biol. Chem.,* 270, 22412-22416.

Pons, S., Asano, T., Glasheen, E., Miralpeix, M., Zhang, Y., Fisher, T. C., Meyers Jr, M. G., Sun, X. J. and White, M. W. (1995) The structure and function of p55$^{PIK}$ reveal a new regulatory subunit for phosphatidylinositol 3-kinase. *Mol. Cell. Biol.,* 15, 4453-4465.

Reif, K., Gout, I., Waterfield, M. D. and Cantrell, D. A., (1993) Divergent regulation of phosphatidylinositol 3-kinase P85 alpha and P85 beta isoforms upon T cell activation. *J. Biol. Chem.,* 268, 10780-10788.

Rodriguez-Viciana, P., Wame, P. H., Dhand, R., Vanhaesebroeck, B., Gout, I., Fry, M. J., Waterfield, M. D. and Downward, J. (1994) Phosphatidylinositol-3-OH kinase as a direct target of Ras. *Nature,* 370, 527-532.

Rodriguez-Viciana, P., Wame, R., Vanhaesebroeck, Waterfield, M. D. and Downward, J. (1996) Activation of phosphoinositide 3-kinase by interaction with Ras and by point mutation. *EMBO J.,* 15, 2442-2451.

Sackmann, E. (1994) Membrane bending energy concept of vesicle- and cell-shapes and shape-transitions. *FEBS lett.,* 346, 3-16.

Sainio et al., (1994). Cell. Mol. Neurobiol. 14(5), 439-457.

Shepherd, P., Reaves, B. and Davidson, H. W. (1996) Phosphoinositide 3-kinases and membrane traffic. *Trends Cell. Biol.,* 6, 52-57.

Springer, T. A. (1994) Traffic signals for lymphocyte recirculation and leucocyte emigration: the multistep paradigrm. *Cell,* 76, 301-314.

Stack, J. H., Horazdovsky, B. and Emr, S. D. (1995) Receptor-mediated protein sorting to the vacuole in yeast: roles for a protein kinase, a lipid kinase and GTP-binding proteins. *Annu. Rev. Cell. Dev. Biol.,* 11, 1-33.

Stephens, L. R., Hawkins, P. T. and Downes, C. P. (1989) Metabolic and structural evidence for the existence of a third species of polyphosoinositide in cells: D-phosphatidyl-mvoinositol 3-phosphate. *Biochem. J.,* 259, 267-276.

Stephens, L. R., Huges, K. T. and Irvine, R. F. (1991) Pathway of phosphatidylinositol (3,4,5)-trisphosphate synthesis in activated neutrophils, *Nature,* 351, 33-39.

Stephens, L. R., Jackson, T. R. and Hawkins, P. T. (1993) Agonist-stimulated synthesis of phosphatidylinositol(3,4,5)-triphosphate: a new intracellular signalling system? *Biochim. Biophys. Acta*, 1179, 27-75.

Stephens, L., Smrcka, A., Cooke, F. T., Jackson, T. R., Sternweiss, P. C. and Hawkins, P. T. (1994) A novel phosphoinositide 3 kinase activity in myeloid-derived cells is activated by G protein βγ subunits. *Cell*, 77, 83-93.

Stephens, L., Hawkins, P. T., Eguinoa, A. and Cooke, F. (1996) A heterotrimeric GTPase-regulated isoform of PI3K and the regulation of its potential effectors. *Phil. Trans. R. Soc. Lond.*, 351, 211-215.

Stoyanov, B., Volinia, S., Hanck, T., Rubio, I., Loubtchenkov, M., Maiek, D., Stoyanova, S., Vanhaesebroeck, B., Dhand, R., Nurnberg, B., Gierschik, P., Seedorf, K., Hsuan, J. J., Waterfield, M. D. and Wetzker, R. (1995) Cloning and characterisation of a G protein-activated human phosphoinositide 3-kinase. *Science*, 269, 690-693.

Summers, M. D. and Smith H. E. (1987) A manual of methods for baculovirus vectors and insect cell culture procedures. *Texas Agri. Exp. Station Bull*. No 1555.

Taga, T. and Kishimoto, T. (1995) Sicnalling mechanisms through cytokine receptors that share signal transducing, receptor components. *Curr. Opin. Immunol.*, 7, 17-23.

Tanti, J.-F., Gremaux, T., Van Obbergehen, E. and Le Marchand-Brustei, Y. (1994) Insulin receptor substrate 1 is phosphorylated by the serine kinase activity of phosphatidylinositol 3-kinase. *Biochem. J.*, 304, 17-21.

Taylor, S. S., Knighton, D. R., Zheng, J., Ten Eyck, L. F. and Sowadski, J. M. (1992) Structural framework for the protein kinase family. *Annu. Rev. Cell Biol.*, 8, 429-462.

Toker, A., Meyer, M., Reddy, K. K., Falck, J. R., Aneja, R., Aneja, S., Parra, A., Burns, D. J., Ballas, L. M. and Cantley, L. C. (1994) Activation of protein kinase C family members by the novel polyphosphoinositides PtdIns-3,4-$P^2$ and PtdIns-3,4,5-$P_3$. *J. Biol. Chem.*, 269, 32358-32367.

Vanhaesebroeck, B., Stein, R. and Waterfield, M. D. (1996) Phosphoinositide 3-kinases and the study of their potential function. *Cancer Surveys*, 27. In press.

Birbasius, J. V., Guilherme, A. and Czech, M. P. (1996) Mouse p170 is a novel phosphatidylinositol 3-kinase containing a C2 domain. *J. Biol. Chem.*, 271, 13304-13307.

Volinia, S., Hiles, I., Ormondroyd, E., Nizetic, D., Antonacci, R., Rocchi, M. and Waterfield, M. (1994) Molecular cloning, cDNA sequence and chromosomal localization of the human phosphatidylinositol 3-kinase p110α (PIK3CA) gene. *Genomics*, 24, 472477.

Volinia, S., Dhand, R., Vanhaesebroeck, B., MacDougall, L. K., Stein, R., Zvelebil, M. J., Domin, J., Panaretou, C. and Waterfield, M. D. (1995) A human phosphatidylinositol 3-kinase complex related to the yeast Vps34p-Vps15p protein sorting system. *EMBO J.*, 14, 3339-3348.

Wagner et al., (1996). Nature Biotechnology, 14, 840-844.

Wang, L-M., Keegan, A. D., Paul, W. E., Heidaran, M. A., Gutkind, J. S. and Pierce, J. H. (1992) IL-4 activates a distince signal transduction cascade from IL-3 in factor-dependent myeloid cells. *EMBO J.*, 11, 4899-4908.

Welham, M. J. and Schrader, J. W. (1992) Steel factor-induced tyrosine phosphorylation in murine mast cells. Common elements with IL-3 induced signal transduction pathways. *J. Immunol.*, 149, 2772-2783.

Welham, M. J., Duronio, V. and Schrader, J. W. (1994a) Interleukin-4-dependent proliferation dissociates $p44^{erk-1}$, $p42^{erk-2}$ and $p21^{ras}$ activation from cell growth. *J. Biol. Chem.*, 269, 5865-5873.

Welham, M. J., Dechert. U., Leslie, K. B., Jirik, F. and Schrader, J. W. (1994b) Interleukin (IL)-3 and Granulocyte/Macrophase colony-stimulating factor, but not IL-4, induce tyrosine phosphorylation, activation and association of SHPTP2 with Grb2 and phosphatidylinositol 3'-kinase. *J. Biol. Chem.*, 269, 23764-23768.

Whitman, M., Downes, C. P., Keller, M., Keller, T. and Cantley, L. (1988) Type I phosphatidylinositol kinase makes a novel inositol phospholipd, phosphatidylinositol-3-phosphate. *Nature*. 332, 644-646.

Wientjes, F. B. Hsuan, J. J., Totty, N. F. and Segal, A. W. (1993) $p_{40}^{phax}$, a third cytosolic component of the activation complex of the NADPH oxidase to contain src homology 3 domains. *Biochem. J.*, 296, 557-561.

Wilson et al., (1989). Cancer Research, 49, p711.

Zhang, J., Zhang, J., Shattil, S. J., Cunningham, M. C. and Rittenhouse, S. E. (1996) Phosphoinositide 3-kinase γ and p85/phosphoinositide 3-kinase in platelets. Relative activation by thrombin receptor or β-phorbol myristate acetate and roles in promoting the ligand-binding function of $\alpha_{IIb}\beta_3$ integrin. *J. Biol. Chem.* 271, 6265-6272.

Zvelebil, M. J., MacDougall, L., Leevers, S., Volinia, S., Vanhaesebroeck, B., Gout, I., Panayotou, G., Domin, J., Stein, R., Koga, H., Salim, K., Linacre, J., Das. P., Panaretou, C., Wetzker, R. and Waterfield, M. D. (1996) Structural and functional diversity of phosphoinositide 3-kinases. *Phil. Trans. R. Soc. Lond.*, 351, 217-233.

---

The invention claimed is:

1. An isolated polypeptide which is encoded by an isolated nucleic acid molecule, wherein the complementary sequence of said isolated nucleic acid molecule hybridizes across its full length, under stringent conditions defined as 50% formamide, 5×SSPE, 5× Denhardts Solution, 0.2% SDS, 200 μ/ml yeast RNA, at 60° C., to the nucleotide sequence set forth in SEQ ID NO: 2, wherein said isolated polypeptide is a lipid kinase, and has autophosphorylating activity.

2. The isolated polypeptide of claim 1, comprising at least one domain which has a proline content of 35-45%.

3. The isolated polypeptide of claim 1, comprising amino acids 292-311 of SEQ ID NO: 1.

4. The isolated polypeptide of claim 1, which is a mammalian polypeptide.

5. The isolated polypeptide of claim 4, which is a human polypeptide.

6. The isolated polypeptide of claim 1, comprising the amino acid sequence encoded by SEQ ID NO: 2.

* * * * *

SEQUENCE LISTING

```
<160> NUMBER OF SEQ ID NOS: 11

<210> SEQ ID NO 1
<211> LENGTH: 1044
<212> TYPE: PRT
<213> ORGANISM: Homo sapiens
<220> FEATURE:

<400> SEQUENCE: 1

Met Pro Pro Gly Val Asp Cys Pro Met Glu Phe Trp Thr Lys Glu Glu
 1               5                  10                  15

Asn Gln Ser Val Val Val Asp Phe Leu Leu Pro Thr Gly Val Tyr Leu
             20                  25                  30
```

-continued

```
Asn Phe Pro Val Ser Arg Asn Ala Asn Leu Ser Thr Ile Lys Gln Leu
         35                  40                  45

Leu Trp His Arg Ala Gln Tyr Glu Pro Leu Phe His Met Leu Ser Gly
 50                  55                  60

Pro Glu Ala Tyr Val Phe Thr Cys Ile Asn Gln Thr Ala Glu Gln Gln
 65                  70                  75                  80

Glu Leu Glu Asp Glu Gln Arg Arg Leu Cys Asp Val Gln Pro Phe Leu
                 85                  90                  95

Pro Val Leu Arg Leu Val Ala Arg Glu Gly Asp Arg Val Lys Lys Leu
                100                 105                 110

Ile Asn Ser Gln Ile Ser Leu Leu Ile Gly Lys Gly Leu His Glu Phe
            115                 120                 125

Asp Ser Leu Cys Asp Pro Glu Val Asn Asp Phe Arg Ala Lys Met Cys
        130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
                180                 185                 190

Asn Val Lys Phe Glu Gly Ser Glu Glu Ser Phe Thr Phe Gln Val Ser
            195                 200                 205

Thr Lys Asp Val Pro Leu Ala Leu Met Ala Cys Ala Leu Arg Lys Lys
        210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
                260                 265                 270

His Leu Thr Met Val His Ser Ser Ile Leu Ala Met Arg Asp Glu
            275                 280                 285

Gln Ser Asn Pro Ala Pro Gln Val Gln Lys Pro Arg Ala Lys Pro Pro
        290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
                340                 345                 350

Met Leu Cys Lys Thr Val Ser Ser Glu Val Ser Val Cys Ser Glu
            355                 360                 365

Pro Val Trp Lys Gln Arg Leu Glu Phe Asp Ile Asn Ile Cys Asp Leu
370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Lys Ser Lys Lys Ala Asp Cys
                405                 410                 415

Pro Ile Ala Trp Ala Asn Leu Met Leu Phe Asp Tyr Lys Asp Gln Leu
                420                 425                 430

Lys Thr Gly Glu Arg Cys Leu Tyr Met Trp Pro Ser Val Pro Asp Glu
            435                 440                 445

Lys Gly Glu Leu Leu Asn Pro Thr Gly Thr Val Arg Ser Asn Pro Asn
```

```
                450             455             460
Thr Asp Ser Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                    485                 490                 495

His Ser Glu Cys Val His Val Thr Glu Glu Gln Leu Gln Leu Arg
            500                 505                 510

Glu Ile Leu Glu Arg Arg Gly Ser Gly Leu Tyr Glu His Glu Lys
        515                 520                 525

Asp Leu Val Trp Lys Leu Arg His Glu Val Gln Glu His Phe Pro Glu
530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
                580                 585                 590

Gly Ser Phe Ala Ile Lys Ser Leu Arg Lys Leu Thr Asp Asp Glu Leu
        595                 600                 605

Phe Gln Tyr Leu Leu Gln Leu Val Gln Val Leu Lys Tyr Glu Ser Tyr
        610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                    645                 650                 655

Val Pro Ser Val Ala Leu Arg Phe Gly Leu Ile Leu Glu Ala Tyr Cys
                660                 665                 670

Arg Gly Arg Thr His His Met Lys Val Leu Met Lys Gln Gly Glu Ala
            675                 680                 685

Leu Ser Lys Leu Lys Ala Leu Asn Asp Phe Val Lys Leu Ser Ser Gln
        690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
                740                 745                 750

Asp Ser Lys Met Lys Pro Leu Trp Ile Met Tyr Ser Asn Glu Glu Ala
            755                 760                 765

Gly Ser Gly Gly Ser Val Gly Ile Ile Phe Lys Asn Gly Asp Asp Leu
        770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815

Pro Thr Gly Asp Arg Thr Gly Leu Ile Glu Val Val Leu Arg Ser Asp
            820                 825                 830

Thr Ile Ala Asn Ile Gln Leu Asn Lys Ser Asn Met Ala Ala Thr Ala
        835                 840                 845

Ala Phe Asn Lys Asp Ala Leu Leu Asn Trp Leu Lys Ser Lys Asn Pro
        850                 855                 860

Gly Glu Ala Leu Asp Arg Ala Ile Glu Glu Phe Thr Leu Ser Cys Ala
865                 870                 875                 880
```

Gly Tyr Cys Val Ala Thr Tyr Val Leu Gly Ile Gly Asp Arg His Ser
                885                 890                 895
Asp Asn Ile Met Ile Arg Glu Ser Gly Gln Leu Phe His Ile Asp Phe
            900                 905                 910
Gly His Phe Leu Gly Asn Phe Lys Thr Lys Phe Gly Ile Asn Arg Glu
        915                 920                 925
Arg Val Pro Phe Ile Leu Thr Tyr Asp Phe Val His Val Ile Gln Gln
    930                 935                 940
Gly Lys Thr Asn Asn Ser Glu Lys Phe Glu Arg Phe Arg Gly Tyr Cys
945                 950                 955                 960
Glu Arg Ala Tyr Thr Ile Leu Arg Arg His Gly Leu Leu Phe Leu His
                965                 970                 975
Leu Phe Ala Leu Met Arg Ala Ala Gly Leu Pro Glu Leu Ser Cys Ser
            980                 985                 990
Lys Asp Ile Gln Tyr Leu Lys Asp Ser Leu Ala Leu Gly Lys Thr Glu
        995                 1000                1005
Glu Glu Ala Leu Lys His Phe Arg Val Lys Phe Asn Glu Ala Leu Arg
    1010                1015                1020
Glu Ser Trp Lys Thr Lys Val Asn Trp Leu Ala His Asn Val Ser Lys
1025                1030                1035                1040
Asp Asn Arg Gln

<210> SEQ ID NO 2
<211> LENGTH: 3387
<212> TYPE: DNA
<213> ORGANISM: Homo sapiens
<220> FEATURE:

<400> SEQUENCE: 2

| | | | | | |
|---|---|---|---|---|---|
| atgccccctg | gggtggactg | ccccatggaa | ttctggacca | aggaggagaa | tcagagcgtt | 60 |
| gtggttgact | tcctgctgcc | cacagggggtc | tacctgaact | tccctgtgtc | ccgcaatgcc | 120 |
| aacctcagca | ccatcaagca | gctgctgtgg | caccgcgccc | agtatgagcc | gctcttccac | 180 |
| atgctcagtg | ccccgaggc | ctatgtgttc | acctgcatca | accagacagc | ggagcagcaa | 240 |
| gagctggagg | acgagcaacg | cgtctctgtg | acgtgcagc | ccttcctgcc | cgtcctgcgc | 300 |
| ctggtggccc | gtgagggcga | ccgcgtgaag | aagctcatca | actcacagat | cagcctcctc | 360 |
| atcggcaaag | cctccacga | gtttgactcc | ttgtgcgacc | cagaagtgaa | cgactttcgc | 420 |
| gccaagatgt | gccaattctg | cgaggaggcg | ccgccccgcc | ggcagcagct | gggctggag | 480 |
| gcctggctgc | agtacagttt | ccccctgcag | ctggagccct | cggctcaaac | ctgggggcct | 540 |
| ggtaccctgc | ggctcccgaa | ccgggccctt | ctggtcaacg | ttaagtttga | gggcagcgag | 600 |
| gagagcttca | ccttccaggt | gtccaccaag | gacgtgccgc | tggcgctgat | ggcctgtgcc | 660 |
| ctgcggaaga | aggccacagt | gttccggcag | ccgctggtgg | agcagccgga | agactacacg | 720 |
| ctgcaggtga | cggcaggca | tgagtacctg | tatggcagct | accgctctg | ccagttccag | 780 |
| tacatctgca | gctgcctgca | cagtggggttg | accctcacc | tgaccatggt | ccattcctcc | 840 |
| tccatcctcg | ccatgcggga | tgagcagagc | aaccctgccc | ccaggtcca | gaaaccgcgt | 900 |
| gccaaaccac | ctcccattcc | tgcgaagaag | ccttcctctg | tgtccctgtg | gtccctggag | 960 |
| cagccgttcc | gcatcgagct | catccagggc | agcaaagtga | acgccgacga | gcggatgaag | 1020 |
| ctggtggtgc | aggccggggct | tttccacgggc | aacgagatgc | tgtgcaagac | ggtgtccagc | 1080 |
| tcggaggtga | gcgtgtgctc | ggagcccgtg | tggaagcagc | ggctggagtt | cgacatcaac | 1140 |

```
atctgcgacc tgccccgcat ggcccgtctc tgctttgcgc tgtacgccgt gatcgagaaa    1200
gccaagaagg ctcgctccac caagaagaag tccaagaagg cggactgccc cattgcctgg    1260
gccaacctca tgctgtttga ctacaaggac cagcttaaga ccggggaacg ctgcctctac    1320
atgtggccct ccgtcccaga tgagaagggc gagctgctga accccacggg cactgtgcgc    1380
agtaacccca cacgcgatag cgccgctgcc ctgctcatct gcctgcccga ggtggccccg    1440
caccccgtgt actaccccgc cctggagaag atcttggagc tggggcgaca cagcgagtgt    1500
gtgcatgtca ccgaggagga gcagctgcag ctgcgggaaa tcctggagcg gcgggggtct    1560
ggggagctgt atgagcacga aaggacctg gtgtggaagc tgcggcatga agtccaggag    1620
cacttcccgg aggcgctagc ccggctgctg ctggtcacca agtggaacaa gcatgaggat    1680
gtggcccaga tgctctacct gctgtgctcc tggccggagc tgcccgtcct gagcgccctg    1740
gagctgctag acttcagctt ccccgattgc acgtaggct ccttcgccat caagtcgctg    1800
cggaaactga cggacgatga gctgttccag tacctgctgc agctggtgca ggtgctcaag    1860
tacgagtcct acctggactg cgagctgacc aaattcctgc tggaccgggc cctggccaac    1920
cgcaagatcg gccacttcct tttctggcac ctccgctccg agatgcacgt gccgtcggtg    1980
gccctgcgct tcggcctcat cctggaggcc tactgcaggg gcaggaccca ccacatgaag    2040
gtgctgatga agcaggggga agcactgagc aaactgaagg ccctgaatga cttcgtcaag    2100
ctgagctctc agaagacccc caagcccag accaaggagc tgatgcactt gtgcatgcgg    2160
caggaggcct acctagaggc cctctcccac ctgcagtccc cactcgaccc cagcaccctg    2220
ctggctgaag tctgcgtgga gcagtgcacc ttcatggact ccaagatgaa gcccctgtgg    2280
atcatgtaca gcaacgagga ggcaggcagc ggcggcagcg tgggcatcat ctttaagaac    2340
ggggatgacc tccggcagga catgctgacc ctgcagatga tccagctcat ggacgtcctg    2400
tggaagcagg agggggctgga cctgaggatg acccccatg gctgcctccc caccggggac    2460
cgcacaggcc tcattgaggt ggtactccgt tcagacacca tcgccaacat ccaactcaac    2520
aagagcaaca tggcagccac agccgccttc aacaaggatg ccctgctcaa ctggctgaag    2580
tccaagaacc cgggggaggc cctggatcga gccattgagg agttcaccct ctcctgtgct    2640
ggctattgtg tggccacata tgtgctgggc attggcgatc ggcacagcga caacatcatg    2700
atccgagaga gtgggcagct gttccacatt gattttggcc actttctggg gaatttcaag    2760
accaagtttg gaatcaaccg cgagcgtgtc ccattcatcc tcacctacga ctttgtccat    2820
gtgattcagc aggggaagac taataatagt gagaaatttg aacggttccg gggctactgt    2880
gaaagggcct acaccatcct gcggcgccac gggcttctct cctccacct cttgccctg    2940 atgcgggcgg caggcctgcc tgagctcagc tgctccaaag acatccagta tctcaaggac    3000
tccctggcac tggggaaaac agaggaggag gcactgaagc acttccgagt gaagtttaac    3060
gaagccctcc gtgagagctg gaaaaccaaa gtgaactggc tggcccacaa cgtgtccaaa    3120
gacaacaggc agtagtggct cctcccagcc ctgggcccaa gaggaggcgg ctgcgggtcg    3180
tggggaccaa gcacattggt cctaaagggg ctgaagagcc tgaactgcac ctaacgggaa    3240
agaaccgaca tggctgcctt ttgtttacac tggttatta tttatgactt gaaatagttt    3300
aaggagctaa acagccataa acggaaacgc ctccttcatg cagcggcggt gctgggcccc    3360
ccgaggctgc acctggctct cggctga                                       3387
```

<210> SEQ ID NO 3

```
<211> LENGTH: 23
<212> TYPE: PRT
<213> ORGANISM: Homo sapiens
<220> FEATURE:

<400> SEQUENCE: 3

Ile Ala Ile Glu Ala Ala Ile Asn Arg Asn Ser Ser Asn Leu Pro Leu
 1               5                  10                  15

Pro Leu Pro Pro Lys Lys Thr
            20

<210> SEQ ID NO 4
<211> LENGTH: 20
<212> TYPE: PRT
<213> ORGANISM: Homo sapiens
<220> FEATURE:

<400> SEQUENCE: 4

Thr Met Pro Ser Tyr Ser Arg Arg  Ile Ser Thr Ala Thr Pro Tyr Met
 1               5                  10                  15

Asn Gly Glu Thr
            20

<210> SEQ ID NO 5
<211> LENGTH: 50
<212> TYPE: PRT
<213> ORGANISM: Homo sapiens
<220> FEATURE:

<400> SEQUENCE: 5

Lys Val Lys  Thr Lys Lys Ser Thr Lys Thr Ile Asn Pro Ser Lys Tyr
 1                5                  10                  15

Gln Thr Ile Arg Lys Ala Gly Lys Val His Tyr Pro Val Ala Trp Val
            20                  25                  30

Asn Thr Met Val Phe Asp Phe Lys  Gly Gln Leu Arg Thr Gly Asp Ile
        35                  40                  45

Thr Leu
    50

<210> SEQ ID NO 6
<211> LENGTH: 34
<212> TYPE: PRT
<213> ORGANISM: Homo sapiens
<220> FEATURE:

<400> SEQUENCE: 6

Lys Gly Arg Lys Gly Ala Lys Glu Glu His Cys Pro Leu Ala Trp Gly
 1               5                  10                  15

Asn Ile Asn Leu Phe Asp Tyr Thr Asp Thr Leu Val Ser Gly Lys Met
            20                  25                  30

Ala Leu

<210> SEQ ID NO 7
<211> LENGTH: 38
<212> TYPE: DNA
<213> ORGANISM: Artificial Sequence
<220> FEATURE:
<223> OTHER INFORMATION: A linker for insertion into insect cell vectors

<400> SEQUENCE: 7 gatcccacc atgccccctg gggtggactg ccccatgg                              38
```

```
<210> SEQ ID NO 8
<211> LENGTH: 38
<212> TYPE: DNA
<213> ORGANISM: Artificial Sequence
<220> FEATURE:
<223> OTHER INFORMATION: A linker for insertion into insect cell vectors

<400> SEQUENCE: 8
aattccatgg ggcagtccac cccaggggge atggtggg                     38

<210> SEQ ID NO 9
<211> LENGTH: 58
<212> TYPE: DNA
<213> ORGANISM: Artificial Sequence
<220> FEATURE:
<223> OTHER INFORMATION: A primer for insertion of a mutation

<400> SEQUENCE: 9
gtgtggccac atatgtgctg ggcattggcg atccgcacag cgacaacatc atgatccg    58

<210> SEQ ID NO 10
<211> LENGTH: 53
<212> TYPE: DNA
<213> ORGANISM: Homo sapiens
<220> FEATURE:

<400> SEQUENCE: 10
ggcccggtgc tcgagaattc tactgcctgt tgtctttgga cacgttgtgg gcc        53

<210> SEQ ID NO 11
<211> LENGTH: 30
<212> TYPE: DNA
<213> ORGANISM: Homo sapiens
<220> FEATURE:

<400> SEQUENCE: 11
gtgtggccac atatgtgctg ggcattggcg                              30
```